US010035870B2

(12) United States Patent
Jaunky et al.

(10) Patent No.: US 10,035,870 B2
(45) Date of Patent: Jul. 31, 2018

(54) COPOLYMERS CONTAINING POLYETHER-POLYSILOXANE MACROMONOMER UNITS, PROCESS OF THEIR PREPARATION AND THEIR USE IN COATING COMPOSITIONS AND POLYMERIC MOULDING COMPOUNDS

(71) Applicant: BYK-Chemie, GmbH, Wesel (DE)

(72) Inventors: Wojciech Jaunky, Wesel (DE); Michael Bessel, Dusseldorf (DE); Jia Cheng, Wesel (DE); Petra Della Valentina, Dinslaken (DE); Marc Eberhardt, Wesel (DE); Mark Heekeren, Sonsbeck (DE); Olaf Muschiolik, Wesel (DE)

(73) Assignee: BYK-Chemie, GmbH, Wesel (DE)

( * ) Notice: Subject to any disclaimer, the term of this patent is extended or adjusted under 35 U.S.C. 154(b) by 0 days.

(21) Appl. No.: 15/578,357

(22) PCT Filed: Apr. 8, 2016

(86) PCT No.: PCT/EP2016/057743
§ 371 (c)(1),
(2) Date: Nov. 30, 2017

(87) PCT Pub. No.: WO2017/036612
PCT Pub. Date: Mar. 9, 2017

(65) Prior Publication Data
US 2018/0155482 A1 Jun. 7, 2018

(30) Foreign Application Priority Data
Aug. 31, 2015 (EP) .................................... 15183208

(51) Int. Cl.
C07F 7/08 (2006.01)
C08F 290/06 (2006.01)
C09D 151/08 (2006.01)
C08G 77/46 (2006.01)
A61K 8/91 (2006.01)
A61Q 19/00 (2006.01)
C08G 77/442 (2006.01)
C08F 299/08 (2006.01)
C08G 77/00 (2006.01)

(52) U.S. Cl.
CPC ............ *C08F 290/068* (2013.01); *A61K 8/91* (2013.01); *A61Q 19/00* (2013.01); *C07F 7/08* (2013.01); *C08F 299/08* (2013.01); *C08G 77/442* (2013.01); *C08G 77/46* (2013.01); *C09D 151/085* (2013.01); *C08F 2800/20* (2013.01); *C08G 77/70* (2013.01)

(58) Field of Classification Search
CPC .................................. C07F 7/08; C08F 299/08
See application file for complete search history.

(56) References Cited

U.S. PATENT DOCUMENTS

| 6,288,129 B1 | 9/2001 | Gruning et al. |
| 6,310,069 B1 | 10/2001 | Kawabata et al. |
| 2003/0022984 A1 | 1/2003 | Kawase et al. |
| 2008/0227871 A1 | 9/2008 | Kim et al. |
| 2009/0299022 A1 | 12/2009 | Ichinohe |

FOREIGN PATENT DOCUMENTS

| DE | 19850507 C1 | 5/2000 | |
| DE | 102005034906 A1 | 2/2007 | |
| EP | 1233031 A2 | 8/2002 | |
| EP | 2 128 164 A1 * | 12/2009 | ................ C07F 7/08 |
| EP | 2128164 A1 * | 12/2009 | |

OTHER PUBLICATIONS

PCT/EP2016/057743—International Search Report, dated May 23, 2016.
PCT/EP2016/057743—International Written Opinion, dated May 23, 2016.
Lee, et al. "Syntheses of poly(methyl methacrylate/poly(dimethyl siloxane) graft copolymers and their surface enrichment of their blend with acrylate adhesiv copolymers," Journal of Applied Polymer Science, Sep. 5, 2002, vol. 86, Iss. 7, pp. 1735-1740. Abstract Only.

* cited by examiner

*Primary Examiner* — Carlos A Azpuru
(74) *Attorney, Agent, or Firm* — Curatolo Sidoti Co., LPA; Joseph G. Curatolo; Salvatore A. Sidoti

(57) ABSTRACT

The invention relates to copolymers obtainable from polyether-polysiloxane containing macromonomers, and a process for preparation thereof. The invention further relates to the use of the copolymers as additives in compositions such as coating compositions and polymeric molding compounds as well as such compositions containing at least one inventive copolymer.

16 Claims, No Drawings ially contain urethane bonds. However, the presence of such urethane groups may lead to high-viscosity products, which is undesired. Further, the use of isocyanate-functional (meth)acrylate monomers is undesired due to their toxicity.

COPOLYMERS CONTAINING POLYETHER-POLYSILOXANE MACROMONOMER UNITS, PROCESS OF THEIR PREPARATION AND THEIR USE IN COATING COMPOSITIONS AND POLYMERIC MOULDING COMPOUNDS

CROSS REFERENCE TO RELATED APPLICATIONS

This application is a national stage application of International Application No. PCT/EP2016/057743, filed 8 Apr. 2016, which claims priority from European Patent Application No. 15183208.6, filed 31 Aug. 2015, which applications are incorporated herein by reference.

The invention relates to copolymers obtainable from polyether-polysiloxane containing macromonomers, and a process for preparation thereof. The invention further relates to the use of the copolymers as additives in compositions such as coating compositions and polymeric moulding compounds as well as such compositions containing at least one inventive copolymer.

STATE OF THE ART

It is known to add additives to coatings and polymeric moulding compounds in order to achieve certain qualities, for example improved levelling, slip, mar and scratch resistance, easy-to-clean properties for furniture varnishes and vehicle finishes. The use of polyacrylate and/or polysiloxane additives is widespread and very diverse.

Paint surfaces are normally not entirely smooth, but instead have a more or less structured surface, which is referred to as waviness or orange-peel structure. These surfaces may be finely structured, with a short wave, or coarsely structured, with a long wave. In the majority of cases, this waviness is unwanted.

It is known that poly(meth)acrylic esters and/or polysiloxanes can be used as levelling promoters for coatings. The polysiloxanes are usually dimethylpolysiloxanes, methylalkylpolysiloxanes or else polyether- or polyester-modified dimethyl- or methyl-alkylpolysiloxanes. As far as the poly(meth)acrylates are concerned, it is preferred to use polymers or copolymers of acrylic acid alkyl esters having an alkyl radical chain length of $C_2$-$C_8$, such as, for example, ethyl acrylate, 2-ethylhexyl acrylate or n-butyl acrylate of various molecular weights. The products used in some cases possess molecular weights of up to 100,000 g/mol. These poly(meth)acrylate (co)polymers used as levelling promoters can be employed as such, or as solutions in organic solvents, or in the form of powders applied, for example, to silica. This is particularly customary in the case of use in powder coatings. The amounts of such products that are used are typically 0.1 to 2 wt.-%, based on the coating formulations.

Polysiloxane-modified polyacrylate hybrid structures can also be used not only to achieve improved surface appearance but also to add functionality to the coating such as easy-to-clean properties. The effect of these products derives from an interface activity at the liquid/air interface, these products undergoing orientation to the interface on account of a certain incompatibility with the actual binder of the coating system. This incompatibility can be increased by raising the polysiloxane content of these polymers. This has the effect of decreasing the surface tension of the coatings and is wanted for example when easy-to-clean properties are the targeted goals, as for example described in U.S. Pat. No. 7,122,599 B2. A disadvantage then, however, is that this incompatibility will impact the adhesion of the next coating layer if there is the intention to recoat the surface after some years of service or in case a repair coating becomes necessary or in case an overcoat is desired.

U.S. Pat. No. 7,122,599 B2 relates to coating compositions having anti-adhesion and dirt repellency properties, these compositions being admixed as additive with from 0.1 to 10% by weight, based on the solids content of the coating composition, of a branched polymer which possesses a weight average molecular weight of from 2000 to 200,000 and comprises a polymeric base polymer and also polysiloxane side chains, having a weight-average molecular weight of between 1000 and 30,000, and whose fraction of the total weight of the branched polymer is from 5 to 25% by weight. While U.S. Pat. No. 7,122,599 B2 in general allows a polyether chain between the polymeric backbone of the additives and the polysiloxane moieties in the side chains, it is not particularly preferred to introduce such polyether moieties, since none of the examples disclosed in U.S. Pat. No. 7,122,599 B2 makes use of such macromonomers. Needless to say that U.S. Pat. No. 7,122,599 B2 is completely silent about the manufacture and use of macromonomers comprising a polyether chain connected to a low molecular weight polysiloxane chain. U.S. Pat. No. 7,122,599 B2 further rather relates to polymeric moulding compounds having anti-adhesion and dirt repellency properties, to which this branched polymer is added as additive in an amount of from 0.1 to 10% by weight, based on the total weight of the polymeric moulding compounds.

U.S. Pat. No. 6,310,169 B1 relates to polysiloxane-polyether based macromonomers having a number average molecular weight of 500 to 100,000. Copolymers prepared from such macromonomers are not disclosed in U.S. Pat. No. 6,310,169 B1. According to U.S. Pat. No. 6,310,169 B1, the polyether segment is introduced in order to achieve a higher resistance of the macromonomers to hydrolysis. Further, the macromonomers disclosed therein are prepared by reacting a mono-OH-functional polysiloxane-polyether macromonomer precursor with an isocyanate-functional (meth)acrylate monomer. The macromonomers disclosed in U.S. Pat. No. 6,310,169 B1 therefore necessarily contain urethane bonds. However, the presence of such urethane groups may lead to high-viscosity products, which is undesired. Further, the use of isocyanate-functional (meth)acrylate monomers is undesired due to their toxicity.

The incompatibility of polysiloxane-modified polyacrylate hybrid structures in binder systems can also be controlled in such a way that a good levelling of the coating is obtained while eliminating the occurrence of surface defects and while having no negative impact on the adhesion of the next coating. One approach at solving this problem is the use of copolymer compositions of specific (meth)acrylic esters and copolymerizable polysiloxane macromonomers as for example disclosed in EP 1 233 031 B1 and EP 1 266 913 B1, respectively:

EP 1 233 031 B1 describes additives for paints and inks which are suitable to be blended in paints and inks for high quality finishing. The additive is characterized by comprising a copolymer having a number-average molecular weight of from 1,000 to 60,000 which is obtained by copolymerizing 2 to 50% by weight of a polydimethylsiloxane having (meth)acryloyloxy groups and a degree of polymerization of 5 to 100 with 98 to 50% by weight of specified (meth)acrylic acid ester(s) which have been heretofore used as flow-and-leveling agents for paints and inks. The agent is effective for imparting flow-and-leveling property to painted or printed surfaces and inhibiting ruptures caused in the surfaces by mist formed in the course of the coating or printing procedure.

EP 1 266 913 B1 provides flow-and-leveling agents for powder coatings which provide the coated surfaces with a flow-and-leveling property by blending into powder coatings taking a serious view of finishing and which improves coating defects such as ruptures and craters to contribute to a rise in the appearance in powder coating. The flow-and-leveling agents described in EP 1266913 B1 are (meth)acrylic acid ester base copolymers containing a tris(trimethylsiloxy)silyl group in a proportion of 2 to 65% by weight and having a number average molecular weight of 1,000 to 60,000.

Problem

While the copolymers of the prior art are able to prevent surface defects without interfering with the paints' recoating properties to some extent, the levelling properties are, however, not satisfying enough.

It was therefore an object of the invention to provide additives and processes for the preparation thereof, which solve the before-mentioned drawbacks of the prior art products The preparation processes for preparing these additives should be suitable to obtain very well-defined structures and the additives are to have good compatibility with industrial coating systems and other polymeric systems. The additives should in particular be apt to alter the surface appearance and the surface properties/functionalities of the coating materials or coatings and/or polymeric moulding compounds in a controlled manner. The additives are to be suitable as levelling agents and are to improve the surface appearance levelling, gloss and/or opalescence of the coating materials or coatings, or polymeric moulding compounds while preventing the occurrence of surface defects. Moreover, the additives are to be able to modify the surface properties or functionalities of the coating materials or coatings and/or the polymeric moulding compounds, such that it is possible to achieve, for example, high surface energy surfaces with good recoatability/overcoatability and at the same time free of surface defects. In order, for example, to favour wettability of such substrate surfaces (such as recoatability for example of primers with themselves; such as overcoatability for example of primers with basecoats), the surface energy of the substrates surfaces has to be increased by the use of these additives. Furthermore, the additives added to impart these improved properties are as far as possible not to impair the other properties of the coating materials or coatings, polymeric moulding compounds, such as mechanical properties, weathering resistance, corrosion protection etc. Therefore the additives to be added are also to be able to display their efficacy in relatively small amounts.

Solution

This object has been solved by the subject-matter of the claims of the present application as well as by the preferred embodiments thereof disclosed in this specification, i.e. by the subject matter described herein.

A first subject-matter of the present invention is thus a (meth)acrylic copolymer, said (meth)acrylic copolymer comprising a. a (meth)acrylic backbone,
b. one or more polyether-polysiloxane side chains attached to the (meth)acrylic backbone,
  i. the side chains having a number average molecular weight in the range of from 200 to 20,000,
  ii. the polysiloxane portion of the side chains having a number average molecular weight in the range of from 147 to <1,000, wherein
  iii. the side chains represent from 0.1 to 95.0 wt.-%, based on the total weight of the copolymer,
wherein the (meth)acrylic copolymer has a weight average molecular weight in the range of from 2,000 to 200,000.

A second subject-matter of the present invention is a process for the preparation of the inventive copolymers: The inventive copolymer can be prepared either by the "macromonomer method", wherein an inventively used polyether-polysiloxane macromonomer—prepared from a functional polyether-polysiloxane macromonomer precursor—containing precisely one polymerizable ethylenically unsaturated group is copolymerized with at least one further monomer ("comonomer"), which contains at least one, preferably precisely one, ethylenically unsaturated group, wherein at least one of the one polymerizable ethylenically unsaturated group of the polyether-polysiloxane macromonomer and of the one polymerizable ethylenically unsaturated groups of the comonomer is a (meth)acrylic group, or by the "grafting to" method", wherein a (meth)acrylic polymer (or (meth)acrylic copolymer) including a (meth)acrylic backbone is formed first by polymerization of at least monomer containing both a (meth)acrylic group and a functional group, wherein the polyether-polysiloxane side chain or side chains are then attached to the formed (meth)acrylic backbone in a polymer analogous reaction via reaction of said functional group with the functional polyether-polysiloxane macromonomer precursor ("grafting to" method).

A third subject-matter of the present invention is a composition comprising at least one inventive copolymer in an additive amount. Said composition preferably contains said at least one inventive copolymer in an amount of from 0.1 to 10 wt.-%, based on the total weight of the solids content of the composition. Preferably, the composition is a coating composition, a moulding compound or a cosmetic formulation.

A fourth subject-matter of the present invention is a use of the inventive copolymers as additives such as a levelling agent and/or a wetting agent in a composition such as coating composition, a moulding compound or a cosmetic formulation. Preferably, said composition contains said at least one inventive copolymer in an amount of from 0.1 to 10 wt.-%, based on the total weight of the solids content of the composition.

It has been surprisingly found that the inventive copolymers are in particular suitable as levelling agents and can be additionally used to improve the surface appearance such as gloss and/or opalescence of the compositions containing these copolymers such as coating compositions and polymeric moulding compounds, while at the same these copolymers are able prevent the occurrence of surface defects such as craters etc. It has been further found in this regard that the inventive copolymers are able to modify said surface appearance and/or, additionally, the surface properties/functionalities of such compositions in a controlled manner.

Additionally, it has been in particular surprisingly found that an incorporation of at least one of the inventive copolymer into compositions such as coating compositions or moulding compounds leads to an increase in the surface energy of the substrate surfaces, to which said compositions are applied, which in turn improves wettability of such substrate surfaces. This in turn facilitates recoatability of for example of primers with themselves or overcoatability of or example of primers with basecoats.

Moreover, it has been surprisingly found that the use of the inventive copolymers does not only not impair any surface properties of compositions, in which they are incorporated, but also does not impair further properties such as mechanical properties, weathering resistance, corrosion protection etc.

Furthermore, it has been surprisingly found that the beneficial properties achieved with the inventive copolymers as outlined hereinbefore are even achieved, when these copolymers are added in only relatively small amounts such as 0.1 to 10 wt.-% to compositions such as coating compositions or moulding compounds, based on the total weight of the solids content of the composition.

Surprisingly, it has been further found that the inventive copolymers have good compatibility with industrial coating systems and other polymeric systems such as moulding compounds.

DETAILED DESCRIPTION OF THE INVENTION

Copolymer

Herein the (meth)acrylic copolymer according to the present invention is also called a "copolymer according to the (present) invention" or an "inventive copolymer". The inventive copolymer is preferably a comb copolymer.

The term "(meth)acrylic" means "acrylic" and/or "methacrylic". Similarly, "(meth)acrylate" means acrylates and/or methacrylates. Therefore, a "(meth)acrylic polymer" in general may be formed from only "acrylic monomers", only "methacrylic monomers" or "acrylic and methacrylic monomers". However, polymerizable monomers other than acrylic and/or methacrylic monomers as e.g. styrene and the like may also be contained in a "(meth)acrylic copolymer". In other words a (meth)acrylic polymer may consist of only acrylic and/or methacrylic monomer units but does not have to. The notation "(meth)acrylate polymer or copolymer" or "(meth)acrylic polymer or copolymer" is intended to mean that the polymer/copolymer (polymer skeleton/backbone) is formed predominantly, i.e. preferably more than 50% or more than 75% of the monomer units used, from monomers having a (meth)acrylate group. In the preparation of a (meth)acrylic copolymer, preferably more than 50% or 75% of the monomers thus have a (meth)acrylate group. However, the use of further monomers as comonomers for its preparation is not excluded.

The inventive (meth)acrylic copolymer has a weight average molecular weight in the range of from 2,000 to 200,000, preferably of from 2,500 to 150,000, more preferably of from 3,000 to 100,000, even more preferably of from 3,500 to 75,000, still more preferably of from 4,000 to 50,000, yet more preferably of from 4,250 to 25,000, in particular of from 4,500 to 15,000, most preferably of from 5,000 to 10,000. In another preferred embodiment, the inventive (meth)acrylic copolymer has a weight average molecular weight in the range of from 3,000 to 175,000, more preferably of from 4,000 to 150,000, even more preferably of from 5,000 to 125,000, still more preferably of from 5,000 to 100,000 or of from 6,000 to 100,000, yet more preferably of from 7,000 to 75,000, in particular of from 8,000 to 60,000, most preferably of from 10,000 to 50,000. The weight average molecular weight of the inventive copolymers is determined according to the method described hereinafter ("Test methods"), i.e. is determined via GPC using polystyrene standards and THF (with 1 volume-% of dibutylamine) as eluent.

An appropriate weight average molecular weight of the inventive copolymer as defined above improves the handling and compatibility of the copolymers, particularly for use as an additive which can then be used as a liquid additive. In case the weight average molecular weight of the copolymer is below 2,000 or exceeds 200,000 then only inferior flow properties, levelling properties, anti-crater properties and/or hydrophilic properties (and thus an inferior recoatability/overcoatability) are observed upon its incorporation into compositions such as coating compositions because its migration/segregation to the surface on the coated substrate-surfaces or surfaces at the coating time is insufficient.

The one or more polyether-polysiloxane side chains are attached to the (meth)acrylic copolymer backbone via (a) covalent bond(s).

The one or more polyether-polysiloxane side chains attached to the (meth)acrylic backbone of the inventive copolymer have a number average molecular weight in the range of from 200 to 20,000, preferably of from 300 to 15,000, more preferably of from 400 to 10,000 or of from 500 to 10,000, even more preferably of from 500 to 7,500, still more preferably of from 600 to 5,000, yet more preferably of from 700 to 2,500, in particular of from 750 to 2,000, most preferably of from 800 to 1,800.

The number average molecular weight of the one or more polyether-polysiloxane side chains attached to the (meth)acrylic backbone of the inventive copolymer is determined according to the method described hereinafter ("Test methods"), i.e. is determined via GPC using polydimethylsiloxane standards and toluene as eluent. The number average molecular weight of the one or more side chains corresponds e.g. to the number average molecular weight of a monohydroxy functional polyether-polysiloxane minus 1 (i.e. minus the weight of a hydrogen atom). Said monohydroxy functional polyether-polysiloxane can either be used as starting material for preparing the macromonomer within the macromonomer method for preparing the inventive copolymer, i.e. before it is bound to a (meth)acrylic monomer, which in turn forms said macromonomer, or is used as grafting component in the grafting reaction. In both methods, the monohydroxy functional polyether-polysiloxane formally "loses" a hydrogen atom.

In case the number average molecular weight of the one or more side chains is below 200 only inferior hydrophilic properties (and thus an inferior recoatability/overcoatability) are observed upon incorporation of the copolymer into compositions such as coating compositions. If the number average molecular weight of the one or more side chains exceeds 20,000 then only inferior flow properties, levelling properties, anti-crater properties and/or hydrophilic properties (and thus an inferior recoatability/overcoatability) are observed upon incorporation of the copolymer into compositions such as coating compositions because its migration/segregation to the surface on the coated substrate-surfaces or surfaces at the coating time is insufficient.

The polysiloxane portion of the one or more polyether-polysiloxane side chains attached to the (meth)acrylic backbone of the inventive copolymer chains has a number average molecular weight in the range of from 147 to <1,000, preferably of from 180 to <1,000, more preferably of from 221 to <1,000, even more preferably of from 250 to <1,000, still more preferably of from 275 to <1,000, yet more preferably of from 300 to <1,000, in particular of from 350 to <1,000, most preferably of from 400 to <1,000 or of from 450 to <1,000. In case more than one polyether-polysiloxane side chain is attached to the (meth)acrylic backbone of the inventive copolymer, the number average molecular weight with respect to the polysiloxane portion, of course, refers to each of these side chains.

The lower limit of 147 of the number average molecular weight results from incorporation of a $(CH_3)_3Si$—O—Si$(CH_3)_2$-disiloxan portion as polysiloxane portion into the polyether-polysiloxane side chain, which is the simplest disiloxane portion, which may be used. The term "polysiloxane portion" preferably includes disiloxane portions as well as trisiloxane portion and (higher) polymeric portions, i.e. polysiloxane portions. The preferred lower limit of 221 of the number average molecular weight results from incorporation of a $(CH_3)_3Si$—O—Si$(CH_3)$—O—Si$(CH_3)_3$-trisiloxan (i.e. a heptamethyltrisiloxane) as polysiloxane portion into the polyether-polysiloxane side chain.

In case the number average molecular weight of the polysiloxane portion of the one or more side chains is 1,000 or more, then only inferior flow properties, levelling properties and/or hydrophilic properties (and thus an inferior recoatability/overcoatibility) are observed upon incorporation of the copolymer into compositions such as coating compositions.

The number average molecular weight of the polysiloxane portion of the one or more polyether-polysiloxane side chains is determined according to the method described hereinafter ("Test methods"), i.e. is determined via GPC using polydimethylsiloxane standards standards and toluene as eluent. Said number average molecular weight corresponds to the number average molecular weight of a mono-Si—H-functional polysiloxane minus 1 (i.e. minus the weight of a hydrogen atom). Said mono-Si—H-functional polysiloxane is used as starting material for preparing the polyether-polysiloxane side chain or side chain unit of the inventive copolymer before the polysiloxane is bound to the polyether of the side chain to be formed. During said reaction, the mono-Si—H-functional polysiloxane formally "loses" a hydrogen atom.

The one or more polyether-polysiloxane side chains attached to the (meth)acrylic backbone of the inventive copolymer represent from 0.1 to 95.0 wt.-%, preferably from 0.2 to 90.0 wt.-%, more preferably from 0.3 to 85.0 wt.-%, even more preferably from 0.4 to 80.0 wt.-%, still more preferably from 0.5 to 70.0 wt.-%, yet more preferably from 0.75 to 60.0 wt.-%, in particular from 1.0 to 50.0 wt.-%, most preferably from 1.5 to 45 wt.-%, or from 2.0 to 40 wt.-%, or from 2.5 to 35 wt.-%, in each case based on the total weight of the copolymer.

In case more than one polyether-polysiloxane side chain is attached to the (meth)acrylic backbone of the inventive copolymer, it is possible to use polyether-polysiloxane side chains of identical length or mixtures of polyether-polysiloxane side chains differing in length.

Preferably, the relative weight ratio of polyether segments and polysiloxane segments in the one more side chains is in the range of from 99:1 to 40:60 or of from 99:1 to 45:55, more preferably in the range of from 95:5 to 45:55 or of from 95:5 to 50:50, even more preferably of from 90:10 to 60:40 or of from 90:10 to 70:30.

Preferably, the amount of the polysiloxane segments within the polyether-polysiloxane side chains of the inventive copolymer does not exceed 60 wt.-%, more preferably does not exceed 55 wt.-%, based on the total weight of the polyether-polysiloxane side chains of the inventive copolymer. Vice versa, preferably, the amount of the polyether segments within the polyether-polysiloxane side chains of the inventive copolymer is not lower than 40 wt.-%, more preferably is not lower than 45 wt.-%, based on the total weight of the polyether-polysiloxane side chains of the inventive copolymer.

Preferably, the inventive copolymer is present in liquid state. The term "liquid state" preferably means that the copolymer is a liquid upon application as additive in compositions such as coating composition, moulding compounds and cosmetic formulations, in particular when used as an additive selected from the group consisting of levelling agents, wetting agents, spreading agents, additives to ameliorate overspray acceptance, anti-cratering agents, surface modification agents, emulsifiers, compatibilizers, hydrophilicity increasing agents, antistatic agents and anti-fogging agents. More preferably, the term "liquid state" means that the inventive copolymer is a liquid at standard conditions such as standard temperature and/or standard pressure. Even more preferably, the term "liquid state" means that the inventive copolymer is a liquid at least at a temperature in the range of 273.15 K to 313.15 K and/or at a pressure of 101.325 kPa. In particular, the term "liquid state" means that the inventive copolymer is a liquid at a temperature of 293.15 K and at a pressure of 101.325 kPa.

The inventive copolymer has in particular advantageous properties when it is present in liquid state, especially when it is in liquid state when applied as additive in compositions such as coating composition, moulding compounds and cosmetic formulations, in particular when used as an additive selected from the group consisting of levelling agents, wetting agents, spreading agents, additives to ameliorate overspray acceptance, anti-cratering agents, surface modification agents, emulsifiers, compatibilizers, hydrophilicity increasing agents, antistatic agents and anti-fogging agents. In order to be effectively used as such an additive and/or to achieve at least one of the aforementioned effects such as the modification of surfaces, the copolymer should be preferably able to migrate and orientate at newly created surfaces and interfaces. This is in particular possible when the inventive copolymer is present in liquid state since in this case the inventive copolymer has an even more superior and further increased mobility as compared to copolymers being present in a solid state as described e.g. in DE 10 2005 034 906 A1: The copolymers disclosed in DE 10 2005 034 906 A1 are necessarily provided in solid form. Such copolymers, however, cannot be used as effectively as it is the case for inventive copolymers that are present in liquid state, because the solid copolymers disclosed in DE 10 2005 034 906 A1 cannot readily move to newly created surfaces and interfaces and thus are less effective additives to ameliorate overspray acceptance, anti-cratering agents, surface modification agents, emulsifiers, compatibilizers, hydrophilicity increasing agents, antistatic agents or anti-fogging agents, i.e. are at least not able to achieve the desired properties to the same extent as compared to copolymers being present in liquid form.

Preferably, therefore, the inventive copolymer does not contain any urethane groups. Preferably, no isocyanate functional monomers are used for its preparation.

The inventive copolymers are obtainable by the process(es) for its preparation as outlined hereinafter, in particular by the "macromonomer method" and by the "grafting to method").

Preparation of the Inventive Copolymers and Process(es) for their Preparation

There are in particular two routes which are suitable to obtain the copolymers of the present invention. Both routes are also object of the present invention.

The first route is herein also called the "macromonomer method", while the second route is herein also called the "grafting to method".

The first two steps for preparing the inventive copolymers are identical for each of these two methods, namely a
(a) preparation of the polysiloxane moiety of the one or more polyether-polysiloxane side chains, and a
(b) preparation of a functional polyether-polysiloxane macromonomer precursor for the preparation of the one or more polyether-polysiloxane side chains to be incorporated into the inventive copolymer.

Macromonomers in the sense of the present invention are oligomers or polymers having precisely one unsaturated functional end group, preferably one ethylenically unsaturated end group, in particular one (meth)acrylic end group, through which reaction or (co)polymerization reactions can proceed. Macromonomers are thus macromolecular monomers which can be converted to homo- or copolymers of defined structures. For example, macromonomers having an ethylenically unsaturated end group can be converted by free-radical (co)polymerization to comb polymers having a defined length of the side chains (macromonomer method). Such macromonomers can be obtained from suitable macromonomer precursor components bearing a suitable functional group such as an OH-group (hydroxyl group) or an COOH-group (carboxyl group), which can then react with a suitable unsaturated monomer, e.g. with a (meth)acrylate monomer via a suitable transformation reaction such as a transesterification, wherein the ethylenically unsaturated group of said monomer is retained and incorporated into the formed macromonomer. Such comb polymers are, however, also preparable from polymeric chains such as (meth)acrylic (co)polymer backbones containing functional groups onto which side chains are then grafted or introduced by polymer-analogous reactions by employing a macromonomer precursor component as defined above.

The two different methods are explained in detail hereinafter.

Both the "macromonomer method" and the "grafting to" method encompass a copolymerization step, wherein either
at least one inventively used polyether-polysiloxane macromonomer containing precisely one ethylenically unsaturated group is copolymerized with at least one further monomer as comonomer, which contains at least one ethylenically unsaturated group, wherein at least one of the precisely one ethylenically unsaturated group of the polyether-polysiloxane macromonomer and of the at least one ethylenically unsaturated groups of the comonomer is a (meth)acrylic group ("macromonomer method"),
preferably, wherein the at least one polyether-polysiloxane macromonomer containing precisely one ethylenically unsaturated group is prepared
(i.1) by a transformation reaction of at least one polyether-polysiloxane macromonomer precursor containing precisely one reactive functional group with an ethylenically unsaturated monomer, wherein the ethylenically unsaturated group of said monomer is retained and incorporated into the formed polyether-polysiloxane macromonomer, or
(ii.2) by a transformation reaction of at least one polysiloxane macromonomer precursor containing precisely one Si—H reactive functional group with a polyether macromonomer precursor containing an alpha-ethylenically unsaturated functional group and an omega-ethylenically unsaturated functional group via a hydrosilylation, wherein the hydrosilylation takes place on the alpha-ethylenically unsaturated group of said polyether macromonomer precursor and the omega-ethylenically unsaturated group of said polyether macromonomer precursor is retained and incorporated into the formed polyether-polysiloxane macromonomer,
or
a (meth)acrylic (co)polymer having a (meth)acrylic backbone is formed first by (co)polymerization of at least monomer containing both a (meth)acrylic group and at least one functional group, and the polyether-polysiloxane side chain or side chains are then attached to the formed (meth)acrylic backbone in a polymer analogous reaction, e.g. by transesterification, addition reaction or condensation reaction, via reaction of said at least one functional group with at least one polyether-polysiloxane macromonomer precursor containing precisely one reactive functional group ("grafting to" method).

Preferably, in each case, the copolymerization is a radical copolymerization, in particular a free-radical addition polymerization in a manner known to those skilled in the art. Said free-radical polymerization preferably takes place by means of peroxides or azo compounds as free-radical initiators in organic solvents or in bulk. Suitable solvents include esters, such as ethyl acetate, n-butyl acetate or 1-methoxy-2-propyl acetate, for example, and aromatic solvents, such as toluene or xylene, for example, or else ketones, such as methyl isobutyl ketone or methyl ethyl ketone, for example. The choice of solvent is guided by the later intended use of the copolymer. It is preferred to use low-boiling solvents at atmospheric pressure in order to facilitate the distillative removal of the solvents in the case of applications in which the copolymers are to be used as a 100% product, for example in UV-curing coating compositions. Suitable initiators include peroxides, such as tert-butyl peroxobenzoate or dibenzoyl peroxide, for example. It is also possible, however, to use azo compounds, such as azoisobutyronitrile (AIBN), for example. Peroxides are preferably used.

The radical addition polymerization is preferably conducted at temperatures from 40° C. to 180° C., more preferably from 100° C. to 150° C., with particular preference from 110° C. to 130° C. The radical polymerization can be performed as a continuous or batchwise process. The radical polymerization can be performed, for example, as a bulk polymerization, as a solution polymerization, as a precipitation polymerization, as an emulsion polymerization or as a suspension polymerization. The radical polymerization can be performed as an uncontrolled free-radical polymerization or as a controlled free-radical polymerization. Methods of controlled free-radical polymerization make it possible to achieve better-defined polymer architectures having a narrower molecular weight distribution. It is possible to use the methods known to those skilled in the art for controlled free-radical polymerization, for example ATRP (atom transfer radical polymerization), GTP (group transfer polymerization), NMP (nitroxide mediated polymerization), RAFT (reversible addition fragmentation chain transfer process) or MADIX (macromolecular design via the interchange of xanthates). Controlled polymerization processes include, in particular, the "reversible addition fragmentation chain transfer process" (RAFT), which, in the case of use of particular polymerization regulators, is also referred to as "MADIX" (macromolecular design via the interchange of xanthates) and "addition fragmentation chain transfer". RAFT is described, for example, in Polym. Int. 2000, 49, 993, Aust. J. Chem 2005, 58, 379, J. Polym. Sci. Part A: Polym. Chem. 2005, 43, 5347, Chem. Lett. 1993, 22, 1089, J. Polym. Sci., Part A 1989, 27, 1741 and 1991, 29, 1053 and 1993, 31, 1551 and 1994, 32, 2745 and 1996, 34, 95 and 2003, 41, 645 and 2004, 42, 597 and 2004, 42, 6021, and also in Macromol. Rapid Commun. 2003, 24, 197 and in U.S. Pat. No. 6,291,620, WO 98/01478, WO 98/58974 and WO 99/31144. A further process for controlled polymerization makes use of nitroxyl compounds as polymerization regulators (NMP) and is disclosed, for example, in Chem. Rev. 2001, 101, 3661. Another controlled polymerization process is "group transfer polymerization" (GTP), as disclosed, for example, by O. W. Webster in "Group Transfer Polymerization", in "Encyclopedia of Polymer Science and Engineering", Volume 7, H. F. Mark, N. M. Bikales, C. G. Overberger and G. Menges, Eds., Wiley Interscience, New York 1987, page 580 ff., and in O. W. Webster, Adv. Polym. Sci. 2004, 167, 1-34. Controlled free-radical polymerization using tetraphenylethane, as described, for example, in Macromol. Symp. 1996, 111, 63, is a further example of controlled polymerization. Controlled free-radical polymerization using 1,1-diphenylethene as polymerization regulator is described, for example, in Macromolecular Rapid Communications 2001, 22, 700. Controlled free-radical polymerization using iniferters is disclosed, for example, in Makromol. Chem. Rapid. Commun. 1982, 3, 127. Controlled free-radical polymerization using organocobalt complexes is known, for example, from J. Am. Chem. Soc. 1994, 116, 7973, from Journal of Polymer Science: Part A: Polymer Chemistry, Vol. 38, 1753-1766 (2000), from *Chem. Rev.* 2001, 101, 3611-3659 and from *Macromolecules* 2006, 39, 8219-8222. A further controlled polymerization technique is degenerative chain transfer using iodine compounds as described, for example, in Macromolecules 2008, 41, 6261 or in U.S. Pat. No. 7,034,085. Controlled free-radical polymerization in the presence of thioketones is described, for example, in Chem. Commun., 2006, 835-837 and in Macromol. Rapid Commun. 2007, 28, 746-753. The copolymers can be random copolymers, block copolymers or gradient copolymers.

To influence the weight average molecular weight of the inventive copolymers and the molecular weight distribution of these copolymers, it is possible to use suitable control or chain transfer reagents. Examples include thiols such as n-octyl mercaptan, n-dodecyl mercaptan or t-dodecyl mercaptan and dimers of alpha-methylstyrene. For example, it is possible also to use small amounts of difunctional monomers (e.g. hexanediol diacrylate) in the polymerization in order to increase the weight average molecular weight in a controlled manner.

As outlined hereinbefore, the first two steps for preparing the inventive copolymers are identical for each of the two methods named above, and involve a
  (a) preparation of the polysiloxane moiety of the one or more polyether-polysiloxane side chains, and a
  (b) preparation of a functional polyether-polysiloxane macromonomer precursor for the preparation of the one or more polyether-polysiloxane side chains to be incorporated into the inventive copolymer.

Step (a)—Preparation of the Polysiloxane Moiety of the Polyether-Polysiloxane Side Chains In a first step a mono-Si—H functional polysiloxane of defined molecular weight, i.e. of a molecular weight such that the polysiloxane portion of the one or more side chains when incorporated into the inventive copolymer has a number average molecular weight in the range of from 147 to <1,000, is produced, i.e. a mono-Si—H functional polysiloxane having a number average molecular weight of from 148 to 1000. The silicon atom to which the hydrogen atom is covalently bound can either be at a terminal position (end position) of the polysiloxane, or at a position along the polysiloxane chain.

Preferably, the mono-Si—H functional polysiloxane used for preparation of the polysiloxane moiety of the one or more polyether-polysiloxane side chains of the inventive copolymer is a polysiloxane of below depicted Formula (I):

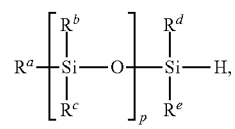

Formula (I)

wherein
parameter p is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, $R^a$, $R^b$, $R^c$, $R^d$ and $R^e$ independently of one another represent
  a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
  a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
  an aryl group with 6 to 30 carbon atoms, preferably with 6 to 15 carbon atoms, an alkylaryl group or arylalkyl group, in each case with 7 to 30 carbon atoms, preferably with 7 to 20 carbon atoms, or
  an alkoxyalkyleneoxide residue or an alkoxypolyalkyleneoxide residue, wherein the alkylene unit is in each case preferably a $C_2$-$C_4$, more preferably an $C_2$- and/or $C_3$-alkylene unit, such as e.g. —$(CH_2)_3$—O—[$(CH_2)_{2-3}$—O]$_r$—$CH_3$, wherein r is 1 to 10, and wherein
$R^d$ may additionally represent —[O—Si($R^b$)($R^c$)]$_q R^a$, wherein $R^a$, $R^b$ and $R^c$ have independently of one another the above defined meanings, and parameter q is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, and $R^e$ may additionally represent —[O—Si($R^b$)($R^c$)]$_o R^a$, wherein $R^a$, $R^b$ and $R^c$ have independently of one another the above defined meanings, and parameter o is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, wherein the sum of p and q and o is at least=1, preferably at least=2, preferably at least=3 or =4.

Of course, the polysiloxane portion of the one or more side chains to be incorporated into the inventive copolymer, which polysiloxane portion is obtainable from a compound of formula (I), must have in total a number average molecular weight in the range of from 147 to <1,000.

Preferably,
parameter p is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9,
$R^a$ represents
a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms,
an alkylaryl group or arylalkyl group, in each case with 7 to 30 carbon atoms, preferably with 7 to 20 carbon atoms, or
an alkoxyalkyleneoxide residue or an alkoxypolyalkyleneoxide residue, wherein the alkylene unit is in each case preferably a $C_2$-$C_4$, more preferably an $C_2$- and/or $C_3$-alkylene unit, such as e.g. —$(CH_2)_3$—O—$[(CH_2)_{2-3}$—O$]_r$—$CH_3$, wherein r is 1 to 10,
and
$R^b$, $R^c$, $R^d$ and $R^e$ independently of one another represent a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms,
an alkylaryl group or arylalkyl group, in each case with 7 to 30 carbon atoms, preferably with 7 to 20 carbon atoms, and wherein
$R^d$ may additionally represent —[O—Si($R^b$)($R^c$)]$_q$$R^a$, wherein $R^a$, $R^b$ and $R^c$ have independently of one another the above defined meanings, and parameter q is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, and
$R^e$ may additionally represent —[O—Si($R^b$)($R^c$)]$_o$$R^a$, wherein $R^a$, $R^b$ and $R^c$ have independently of one another the above defined meanings, and parameter o is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9,
wherein the sum of p and q and o is at least=1, preferably at least=2, preferably at least=3 or =4.

In particular, the mono-Si—H functional polydialkylsiloxane is a mono-Si—H functional polydimethylsiloxane including e.g. heptamethyltrisiloxane.

A person skilled is aware of methods of preparation for compounds of formula (I) and in particular mono-Si—H functional polydialkylsiloxanes. For example, such mono-Si—H functional polydialkylsiloxanes can be produced by a living polymerization of cyclic siloxanes, such as hexamethylene cyclotrisiloxane. The termination can be e.g. achieved by use of a silane as exemplified below in Scheme 1. Such method is e.g. disclosed by Suzuki in Polymer, 30 (1989) 333, in WO 2009/086079 A2, EP 1 985 645 A2 and US 2013/0041098 A1.

Scheme 1

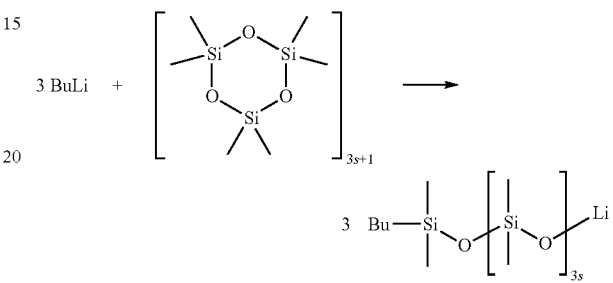

The functionalization of the end group, i.e. formation of the single Si—H-bond can then be performed by reaction with e.g. chlorosilanes, such as dimethylchlorosilane as illustrated below in Scheme 2:

Scheme 2.

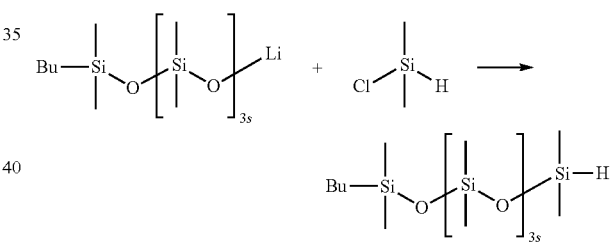

Step (b)—Preparation of a Functional Polyether-Polysiloxane Macromonomer Precursor for the Preparation of the One or More Polyether-Polysiloxane Side Chains to be Incorporated into the Inventive Copolymer The polyether-polysiloxane side chains to be incorporated into the inventive copolymer can be preferably generated by reacting one or more mono-unsaturated, preferably one or more mono-ethylenically unsaturated polyethers, which additionally bear precisely one functional group FG, with one or more mono-Si—H functional polysiloxanes, preferably by hydrosilylation. Said functional group FG is preferably selected from the group consisting of OH-groups, COOH-groups, epoxy groups, isocyanate groups, primary and secondary amino groups, is more preferably selected from the group consisting of OH-groups, COOH-groups, epoxy groups, and primary and secondary amino groups, is even more preferably selected from the group consisting of OH-groups, COOH-groups and epoxy groups, is most preferably selected from the group consisting of OH-groups and COOH-groups. An OH-group as functional group FG is in particular preferred. The functional group FG is preferably a terminal functional group. In a preferred embodiment, FG is not an isocyanate group. The product obtained is a precursor for incorporating said one or more polyether-polysiloxane side chains into the inventive copolymer.

Typical hydrosilylation catalysts are selected from noble metals and their compounds as for example platinum, rhodium and palladium and their compounds. In particular useful are platinum compounds like chloroplatinic acid and their alcoholic solutions, platinum complexes of aliphatic unsaturated hydrocarbons or platinum vinylsiloxane complexes. However platinum black or platinum adsorbed on activated carbon can also be used. A typical amount of platinum is for example an amount of 1 to 50 ppm.

Typical hydrosilylation conditions are as follows. The mono-SiH-functional polysiloxane is put into the reaction vessel first at room temperature such as 23° C. The contents are heated under nitrogen atmosphere to a temperature of 85 to 140° C. A hydrosilylation catalyst, e.g. Karsteds catalyst or any other of the above mentioned catalysts is added. Depending on the extent of the exothermic reaction a part or the complete amount of the monoethylenically unsaturated polyether is added. The reaction should preferably be kept at a temperature ranging between 90 and 120° C. The course of the reaction can be monitored by gasometric determination of residual Si—H groups in the product or by infrared spectroscopy (absorption of Si—H at 2150 cm$^{-1}$). The final polyether-polysiloxane adduct should preferably contain no Si—H groups.

The mono-ethylenically unsaturated polyether used in the hydrosilylation is preferably a mono-vinyl or mono-allyl functional polyether. Said mono-ethylenically unsaturated polyether additionally bears said functional group FG such as OH-group.

Preferably, the mono-ethylenically unsaturated and monofunctionalized-functional polyether used is a compound of below depicted formula (II):

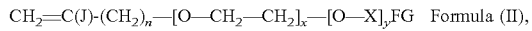

CH$_2$=C(J)-(CH$_2$)$_n$—[O—CH$_2$—CH$_2$]$_x$—[O—X]$_y$FG    Formula (II), wherein
J is H or denotes C$_{1-4}$-alkyl such as methyl,
X is selected from propylene and butylene, preferably X is propylene,
FG is OH, COOH, epoxy, isocyanate, NH$_2$ or NHR$^a$, wherein R$^a$ is C$_{1-8}$-alkyl, preferably is OH, COOH or epoxy, in particular is OH,
n is =0 to 28, preferably 0 or 20 or 1-20, more preferably 0-10 or 1-10, still more preferably 0-5 or 1-5, even more preferably 1 or 2,
x is =1 to 100 or 2-100, preferably 1 to 75 or 2-75, more preferably 1 to 50 or 2-50, even more preferably 1 to 25 or 2-25,
y is =0 to x/3, preferably 0 to x/5, more preferred 0 to x/10 and most preferred 0.

Preferably, the sum of x+y is =1 to 100 or 2-100, more preferably 1 to 50 or 2 to 50.

The ethylene oxide units (—[O—CH$_2$—CH$_2$]$_x$—) and the optionally present propylene/butylene oxide units (—[O—X]$_y$—) can be arranged statistically, as a gradient or in blocks.

Typically, the mono-ethylenically unsaturated polyethers, in particular the one according to formula (II), used in the present invention are water soluble at room temperature, i.e. at a temperature of 18 to 23° C.

Preferred polyether-polysiloxane side chains or, respectively, suitable precursor components for incorporation of these side chains into the (meth)acrylic backbone of the inventive copolymer are obtained by reacting mono-Si—H functional polysiloxanes of formula (I) with mono-ethylenically unsaturated polyethers of general formula (II) in a hydrosilylation reaction.

The reaction product obtainable by such a reaction is preferably a compound of formula (III) as depicted below:

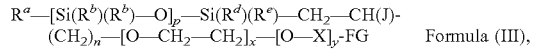

R$^a$—[Si(R$^b$)(R$^b$)—O]$_p$—Si(R$^d$)(R$^e$)—CH$_2$—CH(J)-(CH$_2$)$_n$—[O—CH$_2$—CH$_2$]$_x$—[O—X]$_y$-FG    Formula (III), wherein in each case
R$^a$, R$^b$, R$^c$, R$^d$, R$^e$, p, n, x, X, J, FG and y have the meanings and preferred meanings as defined above in connection with formula (II) and formula (I),
preferably wherein
parameter p is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9,
R$^a$ represents
a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms,
an alkylaryl group or arylalkyl group, in each case with 7 to 30 carbon atoms, preferably with 7 to 20 carbon atoms, or
an alkoxyalkyleneoxide residue or an alkoxypolyalkyleneoxide residue, wherein the alkylene unit is in each case preferably a C$_2$-C$_4$, more preferably an C$_2$- and/or C$_3$-alkylene unit, such as e.g. —(CH$_2$)$_3$—O—[(CH$_2$)$_{2-3}$—O]$_r$—CH$_3$, wherein r is 1 to 10,
and
R$^b$, R$^c$, R$^d$ and R$^e$ independently of one another represent a
a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms,
an alkylaryl group or arylalkyl group, in each case with 7 to 30 carbon atoms, preferably with 7 to 20 carbon atoms,
and wherein
R$^d$ may additionally represent —[O—Si(R$^b$)(R$^c$)]$_q$R$^a$, wherein R$^a$, R$^b$ and R$^c$ have independently of one another the above defined meanings, and parameter q is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, and
R$^e$ may additionally represent —[O—Si(R$^b$)(R$^c$)]$_o$R$^a$, wherein R$^a$, R$^b$ and R$^c$ have independently of one another the above defined meanings, and parameter o is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, wherein the sum of p and q and o is at least=1, preferably at least=2, preferably at least=3 or =4, n is =0 to 28, preferably 0 or 20 or 1-20, more preferably 0-10 or 1-10, still more preferably 0-5 or 1-5, even more preferably 1, x=1 to 100 or 2-100, preferably 1 to 75 or 2-75, more preferably 1 to 50 or 2-50, even more preferably 1 to 25 or 2-25, J is H or denotes $C_{1-4}$-alkyl such as methyl, X is selected from propylene and butylene, preferably is propylene, FG is OH, COOH, epoxy, isocyanate, $NH_2$ or $NHR^a$, wherein $R^a$ is $C_{1-4}$-alkyl, preferably is OH, COOH or epoxy, in particular is OH, y is =0 to x/3, preferably 0 to x/5, more preferred 0 to x/10 and most preferred 0.

Preferably, in general formula (III) the sum of x+y is =1 to 100 or 2-100, more preferably 1 to 50 or 2 to 50.

As stated hereinbefore, the inventive copolymer can be prepared by two processes, namely the "macromonomer method" or by the "grafting to method". The first two steps (a) and (b) as described hereinbefore, are identical for both methods.

"Macromonomer Method"

In the "macromonomer method" an inventively used polymerizable macromonomer has to be formed first: In the "macromonomer method" a macromonomer comprising at least one polyether moiety, at least one polysiloxane moiety and precisely one polymerizable unsaturated group, preferably precisely one ethylenically unsaturated group, i.e. a polyether-polysiloxane macromonomer, is copolymerized in a step (d) with at least one further monomer ("comonomer"), which contains at least one, preferably precisely one, ethylenically unsaturated group, to form the inventive copolymer, wherein at least one of the one polymerizable ethylenically unsaturated groups of the polyether-polysiloxane macromonomer and of the polymerizable ethylenically unsaturated groups of the comonomer is a (meth)acrylic group ("macromonomer method"). Preferably, both the at least one polymerizable unsaturated group of the further monomer ("comonomer") and the one polymerizable unsaturated group of the inventively used macromonomer is a (meth)acrylic group.

According to the macromonomer method, the inventive copolymer is obtainable by radical copolymerization, preferably by free-radical copolymerization, of at least one polysiloxane-polyether macromonomer, i.e. of at least one macromonomer comprising at least one polyether moiety, at least one polysiloxane moiety and precisely one polymerizable ethylenically unsaturated group, and at least one or more than one further radically, preferably free-radically, polymerizable monomer(s) containing at least one, preferably precisely one, ethylenically unsaturated group such as (meth)acrylic group.

Preferably, the inventively used macromonomer does not contain any urethane groups or bonds.

Preferably, in order to provide such a macromonomer comprising at least one polyether moiety, at least one polysiloxane moiety and precisely one polymerizable ethylenically unsaturated group, one or more compounds of formula (III) is/are reacted with a polymerizable ethylenically unsaturated monomer in a step (c) such that the polymerizable ethylenically unsaturated group is maintained in the reaction product, i.e. the macromonomer. Such macromonomers can be e.g. obtained from suitable macromonomer precursor components bearing a suitable functional group such as an OH-group (hydroxyl group) or an COOH-group (carboxyl group), which can then react with a suitable ethylenically unsaturated monomer, e.g. with a (meth)acrylate monomer, via a suitable transformation reaction such as a transesterification, wherein the ethylenically unsaturated group of said monomer is retained and incorporated into the formed macromonomer.

Preferably, said polymerizable ethylenically unsaturated group is introduced into a suitable precursor such as a compound of formula (III) by reacting one or more compounds according to formula (III) obtained from step (b) in a (trans)esterification reaction with a suitable ethylenically unsaturated monomer such as a $(C_1-C_6)$-alkyl (meth)acrylate such as for example methyl methacrylate or n-butyl methacrylate. Instead of using a (trans)esterification reaction it is, of course, also possible to introduce the ethylenically unsaturated groups such as a (meth)acrylic group by using e.g. (meth)acrylic acid in an esterification reaction, or (meth) acryloylchloride and subsequently eliminating H—Cl formed during the reaction, or by reaction with (meth)acrylic anhydride. Preferred are esterification and transesterification reactions.

Alternatively, a suitable other reaction such as e.g. an addition reaction may be performed by reacting a suitable precursor such as a compound of formula (III) obtained from step (b) with a suitable monomer having at least one functional reactive group such as e.g. a functional reactive (meth)acrylic monomer or a functional reactive (meth)allyl or vinyl monomer. A suitable functional reactive monomer is e.g. a monomer such as a (meth)acrylate monomer bearing at least one reactive group such as a hydroxyl, primary or secondary amino group, carboxyl, isocyanate and/or epoxy group. These groups have to be reactive towards the FG-group of the compound according to formula (III). For example, the monomer may contain a carboxyl group or an epoxy groups (such as in the case of a glycidyl ester of (meth)acrylic acid) or an isocyanate group, which then reacts with an OH-group as FG-group of the compound of formula (III). Preferred is the formation of ester bond formed via an OH-groups as FG-group contained in the compound of formula (III) and an carboxylic acid bond contained as reactive functional group in the functional reactive monomer, or vice versa. The use of isocyanate-functional monomers is, however, less desired since the urethane group formed by reaction of OH (as FG) with NCO could lead to high viscosity products. Furthermore the use of isocyanate group containing monomers such as the ones disclosed in U.S. Pat. No. 6,310,169 B1 is undesired due to their toxicity. Preferably, therefore, the inventive copolymer does not contain any urethane groups. Preferably, no isocyanate functional monomers are used for its preparation.

The reaction products obtainable by such reactions according to step (c) can be depicted by formula (IV):

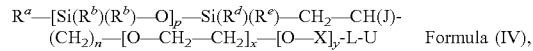
$R^a$—[Si($R^b$)($R^b$)—O]$_p$—Si($R^d$)($R^e$)—CH$_2$—CH(J)-
(CH$_2$)$_n$—[O—CH$_2$—CH$_2$]$_x$—[O—X]$_y$-L-U    Formula (IV), wherein $R^a$, $R^b$, $R^c$, $R^d$, $R^e$, p, n, x, X, J and y have the meanings and preferred meanings as defined above in connection with formula (III), U is an ethylenically unsaturated head group and is preferably selected from the group consisting of vinyl, meth(allyl) and (meth)acryloyl and is more preferably selected from the group consisting of vinyl and (meth)acryloyl and is even more preferably (meth)acryloyl, and L is —O—, —NH—, —C(=O), —C(=O)—O—, —O—C(=O)—, —NH—C(=O), —(C=O)—NH, a linear O—C$_2$-C$_6$-alkyene radical or a branched O—C$_3$-C$_6$-alkylene radical or a O—C$_3$-C$_6$-cycloalkylene radical, preferably is —O—, —NH—, —C(=O), —C(=O)—O— or —O—C(=O)—, more preferably denotes O,
preferably wherein
parameter p is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9,
R$^a$ represents
a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms, an alkylaryl group or arylalkyl group, in each case with 7 to 30 carbon atoms, preferably with 7 to 20 carbon atoms, or
an alkoxyalkyleneoxide residue or an alkoxypolyalkyleneoxide residue, wherein the alkylene unit is in each case preferably a C$_2$-C$_4$, more preferably an C$_2$- and/or C$_3$-alkylene unit, such as e.g. —(CH$_2$)$_3$—O—[(CH$_2$)$_{2-3}$—O]$_r$CH$_3$, wherein r is 1 to 10,
and
R$^b$, R$^c$, R$^d$ and R$^e$ independently of one another represent a
a linear, saturated, halogenated or non-halogenated alkyl group with 1 to 30 carbon atoms, more preferably with 1 to 20 carbon atoms, even more preferably with 1 to 10 carbon atoms, still more preferably, with 1 to 8 carbon atoms, in particular with 1 to 4 carbon atoms, most preferably with 1 to 2 carbon atoms or with 1 carbon atom only,
a branched, saturated, halogenated or non-halogenated alkyl group with 3 to 30 carbon atoms, more preferably with 3 to 20 carbon atoms, even more preferably with 3 to 10 carbon atoms, still more preferably, with 3 to 6 carbon atoms,
an aryl group with 6 to 30 carbon atoms, preferably with 6 to 15 carbon atoms,
an alkylaryl group or arylalkyl group, in each case with 7 to 30 carbon atoms, preferably with 7 to 20 carbon atoms, and wherein
R$^d$ may additionally represent —[O—Si(R$^b$)(R$^c$)]$_q$R$^a$, wherein R$^a$, R$^b$ and R$^c$ have independently of one another the above defined meanings, and parameter q is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9, and
R$^e$ may additionally represent —[O—Si(R$^b$)(R$^c$)]$_o$R$^a$, wherein R$^a$, R$^b$ and R$^c$ have independently of one another the above defined meanings, and parameter o is in the range of from 0 to 11, preferably in the range of from 1 to 11, more preferably in the range of from 1 to 10 or of from 2 to 10 or of from 3 to 10, more preferably in the range of from 1 to 9 or of from 2 to 9 or of from 3 to 9,
wherein the sum of p and q and o is at least=1, preferably at least=2, preferably at least=3 or =4, n is =0 to 28, preferably 0 or 20 or 1-20, more preferably 0-10 or 1-10, still more preferably 0-5 or 1-5, even more preferably 1,
x=1 to 100 or 2-100, preferably 1 to 75 or 2-75, more preferably 1 to 50 or 2-50, even more preferably 1 to 25 or 2-25,
J is H or denotes C$_{1-4}$-alkyl such as methyl,
X is selected from propylene and butylene, preferably is propylene,
y is =0 to x/3, preferably 0 to x/5, more preferred 0 to x/10 and most preferred 0,
U is an ethylenically unsaturated head group and is preferably selected from the group consisting of vinyl, meth(allyl) and (meth)acryloyl and is more preferably selected from the group consisting of vinyl and (meth)acryloyl and is even more preferably (meth)acryloyl, and
L is —O—, —NH—, —C(=O), —C(=O)—O—, —O—C(=O)—, —NH—C(=O), —(C=O)—NH, a linear O—C$_2$-C$_6$-alkyene radical or a branched O—C$_3$-C$_6$-alkylene radical or a O—C$_3$-C$_6$-cycloalkylene radical, preferably is —O—, —NH—, —C(=O), —C(=O)—O— or —O—C(=O)—, more preferably denotes O.

Preferably, in general formula (IV) the sum of x+y is =1 to 100 or 2-100, more preferably 1 to 50 or 2 to 50.

When the at least one polyether-polysiloxane macromonomer of formula (IV) is copolymerized with at least one further monomer as comonomer, which contains at least one ethylenically unsaturated group in order to form the inventive (meth)acrylic copolymer, at least one of the ethylenically unsaturated group U of the polyether-polysiloxane macromonomer of formula (IV) and of the at least one ethylenically unsaturated groups of the comonomer is a (meth)acrylic group.

A particularly preferred compound of Formula (IV) is of Formula (IVa):

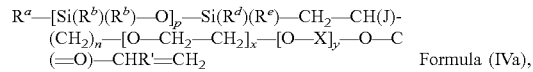

R$^a$—[Si(R$^b$)(R$^c$)—O]$_p$—Si(R$^d$)(R$^e$)—CH$_2$—CH(J)-(CH$_2$)$_n$—[O—CH$_2$—CH$_2$]$_x$—[O—X]$_y$—O—C(=O)—CHR'=CH$_2$    Formula (IVa), wherein
R$^a$, R$^b$, R$^c$, R$^d$, R$^e$, p, n, x, X, J and y have the meanings and preferred meanings as defined above in connection with formula (IV) and R' denotes H or CH$_3$.

A representative example of a monoethylenically unsaturated polyether-polysiloxane macromonomer which can be used to incorporate a polydimethylsiloxane side chain into the inventive copolymer by radical copolymerization via the macromonomer method are for instance, methacryloyloxypolyethylenglycol polydimethylsiloxane, or methacryloyloxypolyethylenglycolpolypropylenepropyl polydimethylsiloxane.

An example of a suitable macromonomer is depicted below:

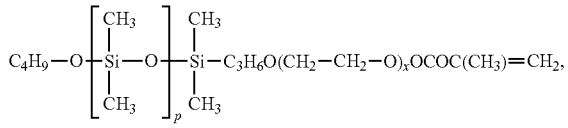

wherein p and x have the meanings and preferred meanings as defined above in connection with formula (IV).

Further examples of a monoethylenically unsaturated polyether-polysiloxane which may be copolymerized as macromonomers into the inventive copolymer are for example, α-butyl-ω-(3-methacryloyloxypolyethylenglycol/ polypropylenepropyl)-polydimethylsiloxane, methacryloyloxypolyethylenglycol/polybutylenepropyl)-polydimethylsiloxane, methacryloyloxypolyethylenglycol/polypropyleneglycol/-polybutyleneglycol) polydimethylsiloxane, whereas the ethylene oxide, propylene oxide and butylene oxide can be arranged in random or block fashion.

It is most preferred that the polymerizable ethylenically unsaturated group is introduced into a suitable precursor such as a compound of formula (III) by reacting one or more compounds according to formula (III) obtained from step (b) in a transesterification reaction with a suitable ethylenically unsaturated monomer such as a ($C_1$-$C_6$)-alkyl (meth)acrylate. Instead of using a transesterification reaction it is, of course, also possible to introduce the ethylenically unsaturated groups such as a (meth)acrylic group by using e.g. (meth)acrylic acid in an esterification reaction, or (meth)acryloylchloride and subsequently eliminating H—Cl formed during the reaction, or by reaction with (meth)acrylic anhydride. Preferred are esterification and transesterification reactions.

Preferably, the reaction of the at least one alkyl (meth)acrylate or (meth)acrylic acid or (meth)acryloylchloride or (meth)acrylic acid anhydride or functional reactive (meth)acrylate with the at least one functional reactive polyether-polysiloxane such as the compound of formula (III) is effected in equal molar amounts or with a molar excess of alkyl (meth)acrylate or (meth)acrylic acid or (meth)acryloylchloride or (meth)acrylic acid anhydride. Preferably, the reaction is effected in a molar ratio of 4:1 to 1:1, the molar ratio being the ratio of the alkyl (meth)acrylate or (meth)acrylic acid or (meth)acryloylchloride or (meth)acrylic acid anhydride or functional reactive methacrylate used to functional polyether-polysiloxane such as the compound of formula (III) used.

The method for synthesizing the polyether-polysiloxane (meth)acrylic esters such as the compounds of formula (IV) by means of a transesterification reaction between an alkyl (meth)acrylate and an hydroxyl functional polyether-polysiloxane such as the one according to formula (III) is done by the known methods of the prior art such as chemical or enzymatic catalysts and under esterification conditions or transesterification conditions common in the art.

For example the transesterification can be made in the presence of a common transesterification chemical catalyst(s), for example, selected from the group consisting of combinations of alkali metal salts of organic or inorganic acids with hydroxides. Preferred chemical catalyst(s) chosen from the list comprising zirconium acetylacetonates, lithium acetylacetonates, calcium acetylacetonates, dibutyltin oxide, distannoxanes and caesium carbonate, used alone or as a mixture.

The esterification can further, for example, been carried out in the presence of an acid or of coupling reagents of the Mitsunobu type, e.g. N,N'-dicyclohexylcarbodiimide (DCC) or 1,1'-carbonyl-diimidazole (GDI) (coupling reagents of the Mitsunobu type are well known to the person skilled in the art and are described, for example, in Progress in the Mitsunobu reaction. A review. Org. Prep. Proced. Int. (1996), 28(2), 127-64 or in The Mitsunobu reaction. Org. React. (N. Y.) (1992), 42 335-656.

An enzymatic (trans)esterification is also possible to prepare the macromonomers of the present invention. Examples of enzymatic catalysts are hydrolases, especially esterases, lipases and proteases as described in the International Publication WO03/074718 A1.

Enzymes which can be employed are hydrolases, especially esterases, lipases and proteases as described by U. T. Bornscheuer, R. T. Kazlauskas in Hydrolases in Organic Synthesis; Wiley-VCH, 1999. page 65-195, ISBN 3-527-30104-6. Specific examples of esterases are those obtained from animals such as horse liver esterase, pig liver esterase, pig pancreas esterase, fungal esterases or esterases from microorganisms such as from *Bacillus subtilis* or from *Pichia polimorpha; Rhizopus* sp. -esterases, *Penicillium* sp. -esterases or yeast esterases or from *Candida* species, *Alcaligene* species or *Pseudomonas* species. Lipases suitable for use herein include those of animal, plant and microbiological origin. Suitable lipases are also found in many strains of bacteria and fungi. Specific examples are porcine pancreatic lipase (PPL), (*G. candidum* (GCL), *H. lanuginosa* (HLL). *Rhizopus* sp. (RML, ROL), *Candida* sp. (CAL-A, CAL-B, CCL), *Aspergillus* sp. (ANL), *Pseudomonas* sp. (PCL, PFL) *Burholderia* sp. (lipase QLM).

Examples of suitable proteolytic enzymes are the subtilisins, thermitase, chymotrypsin, thermolysin, papain, aminoacylasen, penicillin amidases or trypsin. Suitable enzymes are known to those skilled in the art and are not limited to the ones mentioned above.

The enzymes can be employed as crude extracts, in pure form or in immobilized form crude or pure, on a support on which they are bound chemically or physically. Suitable supports are for example silica gel, diato ite, polyacrylamide, Duolite®, Celite®, Eupergit® (Röhm & Haas, Darmstadt, Deutschland) and the like. The enzymes can also be employed as cross-linked-enzymes (CLECs), which enzymes may be obtained from Altus Corp. Suitable enzyme employments are well known and are described, for example, by U. T. Bornscheuer, R. T. Kazlauskas in Hydrolases in Organic Synthesis; Wiley-VCH, 1999. page 61-64, ISBN 3-527-30104-6, or by K. Faber in Biotrans-formation in Organic Chemistry, Springer 1997, 3rd Ed., 345-357, ISBN 3-540-61688-8; H.-J. Rehm, G. Reed In Biotechnology, VCH 1998, $2^{nd}$ Ed. 407-411. Preferred are enzymes that are commercially available (Fluka, Sigma, Novo, Amarro, Roche etc) or enzymes that are well known and described, for example, by H.-J. Rehm, G. Reed in Biotechnology, VCH 1998. $2^{nd}$ Ed., page 40-42.

Especially preferred are immobilized lipases, that are thermostable such as Novozyme 435 (recombinante *Candida antarctica* lipase B (E. M. Anderson et al. Biocat. Biotransf. 1998, 16, 181), (*Firma* NOVO Nordisk, Bagswaerd, Danemark)) or the enzyme QLM, QL (Meito Sangyo, Japan).

Enzymes having esterase, lipase and/or protease activity may be obtained from natural sources and/or from microorganism using standard procedures known in the art, for example from cloning processes via expression and amplification.

The methods, conditions and procedures of chemical and enzymatic (trans)esterification reactions useful to prepare the macromonomers such as the compounds of formula (IV) and copolymers of the present invention are described in patents WO 2009/071786 A1 and EP 0 999 230 B1.

The (trans)esterification may optionally be conducted in the presence of a polymerisation inhibitor. Examples of suitable inhibitors of polymerization are hydroquinone, hydroquinone monomethyl ether, 4-hydroxy-2,2,6,6-tetramethyl-1-piperidinyloxy (4-hydroxy-TEMPO) or phenothiazines. The inhibitor of polymerization is used to scavenge free radicals which possibly form during the thermally promoted ester bond formation or in the course of storage of the macromonomers, such that the stability of the ethylenically unsaturated polymerizable group is ensured. It is thus an advantage of the use of an inhibitor of polymerization that the reaction is facilitated and a lower level of by-products such as homooligomers or homopolymers occurs. The (trans)esterification may be conducted in the absence of an inhibitor of polymerization when a lower temperature is used such as in the case of an enzymatic (trans)esterification.

It is possible to use solvents in the (trans)esterification reaction. Suitable solvents for the (trans)esterification reaction do not affect negatively interfer with the (trans)esterification reaction. Examples of suitable solvents are those which do not contain any active hydrogen atoms which could give unwanted reactions. Preference is given to using aliphatic, cycloaliphatic, aromatic hydrocarbons such as, for example, cyclohexane, benzene, toluene or xylene, ketones and cyclic ethers, as solvents. The choice of solvent is also guided by the later end use of the inventive macromonomer and copolymer to be synthesized subsequently from the macromonomers. Preference is given to using low-boiling solvents in order to facilitate their distillative removal.

At the end of the reaction, the product is cooled. Solvents and polymerization inhibitors can be removed if required prior to the subsequent copolymerization by suitable distillation or filtration measures. The transesterification can also be carried out in the absence of solvents and polymerization inhibitors.

As a further alternative, the inventively used polymerizable macromonomer, i.e the at least one polyether-polysiloxane macromonomer containing precisely one ethylenically unsaturated group such as a macromonomer of Formula (IV) or (IVa), can be obtained in a different manner, namely by a transformation reaction of at least one polysiloxane macromonomer precursor containing precisely one Si—H reactive functional group such as a polysiloxane of Formula (I) as described hereinbefore with a suitable polyether macromonomer precursor, i.e. a precursor containing an alpha-ethylenically unsaturated functional group (to be reacted with said Si—H-group) and an omega-ethylenically unsaturated functional group via a hydrosilylation reaction, wherein the hydrosilylation takes place on the alpha-ethylenically unsaturated group of said polyether macromonomer precursor and the omega-ethylenically unsaturated group of said polyether macromonomer precursor is retained and incorporated into the formed polyether-polysiloxane macromonomer.

A suitable polyether macromonomer precursor, i.e. a precursor containing an alpha-ethylenically unsaturated functional group and an omega-ethylenically unsaturated functional group, can be represented by below depicted Formula (V):

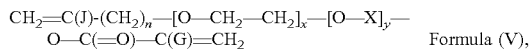

Formula (V), wherein
J is H or denotes $C_{1-4}$-alkyl such as methyl, preferably denotes H,
X is selected from propylene and butylene, preferably X is propylene,
G denotes H or denotes $C_{1-4}$-alkyl such as methyl, preferably denotes $C_{1-4}$-alkyl such as methyl,
n is =0 to 28, preferably 0 or 20 or 1-20, more preferably 0-10 or 1-10, still more preferably 0-5 or 1-5, even more preferably 1 or 2,
x is =1 to 100 or 2-100, preferably 1 to 75 or 2-75, more preferably 1 to 50 or 2-50, even more preferably 1 to 25 or 2-25,
y is =0 to x/3, preferably 0 to x/5, more preferred 0 to x/10 and most preferred 0.

Preferably, the sum of x+y is =1 to 100 or 2-100, more preferably 1 to 50 or 2 to 50.

The alpha-ethylenically unsaturated group of the component of Formula (V) is the $CH_2$=C(J)-group. The omega-ethylenically unsaturated group of the component of Formula (V) is the —C(G)=$CH_2$-group. The nomenclature "alpha" and "omega" in this respect corresponds to a commonly used convention.

For example, an inventively used macromonomer of Formula (IV) can be obtained by the following reaction:

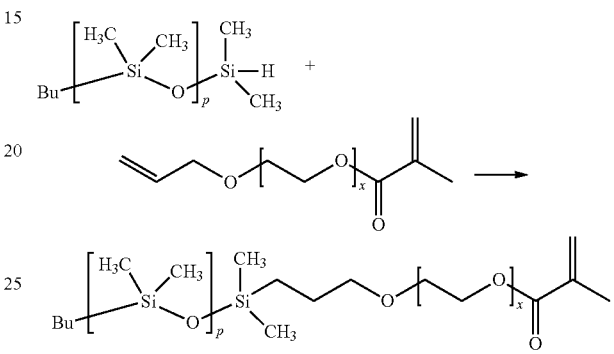

A compound of Formula (V) is in turn e.g. obtainable by a transesterification reaction of a compound of Formula (III) with a suitable compound having both an ester function to be used for the transesterification and precisely one ethylenically unsaturated group. In the above depicted example, e.g. an allyl polyethylene glycol can be used as an example of a compound of Formula (III) and methyl methacrylate as an example of compound having an ester function and precisely one ethylenically unsaturated bond.

Using the macromonomer method macromonomers as exemplified in formulae (IV) and (IVa) are reacted with one or more further polymerizable monomers ("comonomers") such as ethylenically unsaturated monomers, in particular (meth)acrylates, to form the target copolymer of the present invention in a step (d). Preferably, at least 85% by weight, preferably at least 90% by weight, more preferably at least 95% by weight and even more preferred at least 98 or 99% or 100% by weight of the comonomers used to prepare the copolymer of the invention have only one polymerizable double bond.

One or more ethylenically unsaturated polymerizable comonomers as said ethylenically unsaturated monomers other than the above-described macromonomer(s) such as the compounds of formulae (IV) and (IVa) are used in step (d). Polymerizable comonomers are understood to mean those compounds which bear at least one polymerizable group. Polymerizable groups are understood to mean functional groups which can be polymerized under conditions customary therefore, for example ethylenically unsaturated groups such as (meth)acrylic groups.

Examples of ethylenically unsaturated polymerizable comonomers are as follows:
a1) essentially acid-group-free (meth)acrylic esters such as (meth)acrylic alkyl or cycloalkyl esters including having up to 22 carbon atoms, preferably 1 to 22 carbon atoms, in the (cyclo)alkyl radical, including alkyl acrylates and alkyl methacrylates of straight-chain alcohols having 1 to 22 carbon atoms or branched or cycloaliphatic alcohols having 3 to 22 carbon atoms, aralkyl acrylates and aralkyl methacrylates of aralkyl alcohols having 8 to 18 carbon atoms, wherein alkyl radical is linear or branched, preferably linear, especially methyl, ethyl, propyl, n-butyl, sec-butyl, tert-butyl, hexyl, ethylhexyl, stearyl and lauryl acrylate or methacrylate; cycloaliphatic (meth)acrylic esters, especially cyclohexyl, isobornyl, dicyclopentadienyl, octahydro-4,7-methano-1H-indenemethanol or tert-butylcyclohexyl (meth)acrylate; (meth)acrylic oxaalkyl esters or oxacycloalkyl esters such as ethyltriglycol (meth)acrylate and methoxyoligoglycol (meth)acrylate, or other ethoxylated and/or propoxylated hydroxyl-free (meth)acrylic acid derivatives such as polyethylene glycol mono(meth)acrylates having from 5 to 80 carbon atoms, for example methoxypolyethylene glycol monoacrylate, and methoxypolyethylene glycol monomethacrylate. These may contain minor amounts of (meth)acrylic alkyl or cycloalkyl esters of higher functionality, such as the di(meth)acrylates of ethylene glycol, propylene glycol, diethylene glycol, dipropylene glycol, butylene glycol, 1,5-pentanediol, 1,6-hexanediol, octahydro-4,7-methano-1H-indenedimethanol or 1,2-, 1,3- or 1,4-cyclohexanediol; trimethylolpropane di- or tri(meth)acrylate; or pentaerythritol di-, tri- or tetra(meth)acrylate; maleic esters, itaconic esters and fumaric esters of straight-chain alcohols having 1 to 22 or branched or cycloaliphatic alcohols having 3 to 22 carbon atoms; fluorinated and fluorine-free alkyl esters of methacrylic acid, of maleic acid, of fumaric acid, of itaconic acid and of mesaconic acid (methylfumaric acid), methacrylic acid, acrylic acid, a2) Monomers which carry per molecule at least one hydroxyl group, amino group, alkoxymethylamino group or imino group and are essentially free from acid groups, such as hydroxyalkyl esters of acrylic acid, methacrylic acid, preferably hydroxyalkyl (meth)acrylates of straight-chain diols having 2 to 36 carbon atoms or branched or cycloaliphatic diols having 3 to 36 carbon atoms, or another alpha,beta-olefinically unsaturated carboxylic acid, which derive from an alkylene glycol esterified with the acid, or which are obtainable by reacting the alpha,beta-olefinically unsaturated carboxylic acid with an alkylene oxide, especially hydroxyalkyl esters of acrylic acid, methacrylic acid, ethacrylic acid, crotonic acid, maleic acid, fumaric acid or itaconic acid in which the hydroxyalkyl group contains up to 20 carbon atoms, such as 2-hydroxyethyl, 2-hydroxypropyl, 3-hydroxypropyl, 3-hydroxybutyl, 4-hydroxybutyl acrylate, methacrylate, ethacrylate, crotonate, maleate, fumarate or itaconate; or hydroxycycloalkyl esters such as 1,4-bis(hydroxymethyl)cyclohexane, octahydro-4,7-methano-1H-indenedimethanol or methylpropanediol monoacrylate, monomethacrylate, monoethacrylate, monocrotonate, monomaleate, monofumarate or monoitaconate; or reaction products of cyclic esters, such as epsilon-caprolactone and/or valerolactone such as caprolactone- and/or valerolactone-modified hydroxyethyl acrylate and caprolactone- and/or valerolactone-modified hydroxy-ethyl methacrylate; or olefinically unsaturated alcohols such as allyl alcohol or polyols such as trimethylolpropane monoallyl or diallyl ether or pentaerythritol monoallyl, diallyl or triallyl ether (as far as these monomers (a2) of higher functionality are concerned, the comments made above relating to the monomers (a1) of higher functionality apply analogously); N,N-dimethylaminoethyl acrylate, N,N-diethylaminoethyl methacrylate, allylamine or N-methyliminoethyl acrylate or N,N-di(methoxymethyl)aminoethyl acrylate and methacrylate or N,N-di(butoxymethyl)aminopropyl acrylate and methacrylate; hydroxyalkyl vinyl ethers such as hydroxybutyl vinyl ether; ethoxylated and/or propoxylated hydroxyl-functional (meth)acrylic acid derivatives such as triethylene glycol monoacrylate, triethylene glycol monomethacrylate, polyethylene glycol monoacrylate, polyethylene glycol monomethacrylate.

a3) Monomers which carry per molecule at least one acid group which can be converted into the corresponding acid anion group, such as acrylic acid, methacrylic acid, ethacrylic acid, crotonic acid, maleic acid, fumaric acid or itaconic acid; olefinically unsaturated sulfonic or phosphonic acids or their partial esters; or mono(meth)acryloyloxyethyl maleate, succinate or phthalate.

a4) Vinyl esters such as vinyl alkanoates having 2 to 30 carbon atoms, vinyl esters such as vinyl acetate, vinyl propionate, vinyl butyrate, vinyl pivalate and/or the vinyl ester of 2-methyl-2-ethylheptanoic acid; vinyl esters of alpha-branched monocarboxylic acids having 5 to 18 carbon atoms in the molecule: The branched monocarboxylic acids can be obtained by reacting formic acid or carbon monoxide and water with olefins in the presence of a liquid, strongly acidic catalyst; the olefins may be cracking products of paraffinic hydrocarbons, such as mineral oil fractions, and may comprise both branched and straight-chain acyclic and/or cycloaliphatic olefins. The reaction of such olefins with formic acid or, respectively, with carbon monoxide and water produces a mixture of carboxylic acids in which the carboxyl groups are located predominantly on a quaternary carbon atom. Examples of other olefinic starting materials are propylene trimer, propylene tetramer and diisobutylene. Alternatively, the vinyl esters (a4) may be prepared in a conventional manner from the acids, by reacting, for example, the acid with acetylene. Particular preference, owing to their ready availability, is given to using vinyl esters of saturated aliphatic monocarboxylic acids having 9 to 11 carbon atoms that are branched on the alpha carbon atom, but especially Versatic® acids.

a5) Reaction products of acrylic acid and/or methacrylic acid with the glycidyl ester of an alpha-branched monocarboxylic acid having 5 to 18 carbon atoms per molecule, especially a Versatic® acid, or, instead of the reaction product, an equivalent amount of acrylic acid and/or methacrylic acid which is then reacted during or after the polymerization reaction with the glycidyl ester of an alpha-branched monocarboxylic acid having 5 to 18 carbon atoms per molecule, especially a Versatic® acid.

a6) Cyclic and/or acyclic olefins, preferably olefins having 2 to 30 carbon atoms and arylalkenes having 8 to 30 carbon atoms such as ethylene, propylene, 1-butene, 1-pentene, 1-hexene, cyclohexene, cyclopentene, norbornene, butadiene, isoprene, cyclopentadiene and/or dicyclopentadiene.

a7) (Meth)acrylamides such as (meth)acrylamide, N-methyl-, N,N-dimethyl-, N-ethyl-, N,N-diethyl-, N-propyl-, N,N-dipropyl-, N-butyl-, N,N-dibutyl-, N-cyclohexyl-, N,N-cyclohexylmethyl- and/or N-methylol-, N,N-dimethylol-, N-methoxymethyl-, N,N-di(methoxymethyl)-, N-ethoxymethyl- and/or N,N-di(ethoxyethyl)-(meth)acrylamide.

a8) Monomers containing epoxide groups, such as the glycidyl esters of acrylic acid, methacrylic acid, ethacrylic acid, crotonic acid, maleic acid, fumaric acid and/or itaconic acid.

a9) Vinylaromatic hydrocarbons such as styrene, alpha-alkylstyrenes, especially alpha-methylstyrene, and/or vinyltoluene; vinylbenzoic acid (all isomers), N,N-diethylaminostyrene (all isomers), alpha-methylvinylbenzoic acid (all isomers), N,N-diethylamino-alpha-methylstyrene (all isomers) and/or p-vinylbenzenesulfonic acid.

a10) Nitriles such as acrylonitrile and/or methacrylonitrile.
a11) Vinyl compounds, especially vinyl halides and/or vinylidene dihalides such as vinyl chloride, vinyl fluoride, vinylidene dichloride or vinylidene difluoride; N-vinylamides such as vinyl-N-methylformamide, N-vinylcaprolactam, 1-vinylmidazole or N-vinylpyrrolidone; vinyl ethers such as ethyl vinyl ether, n-propyl vinyl ether, isopropyl vinyl ether, n-butyl vinyl ether, isobutyl vinyl ether and/or vinyl cyclohexyl ether; vinyl ketones having 3 to 20 carbon atoms,
a12) Allyl compounds, especially allyl ethers and allyl esters such as allyl methyl, ethyl, propyl or butyl ether or allyl acetate, propionate or butyrate.
a13) Acryloxysilane-containing vinyl monomers, preparable by reacting hydroxyl-functional silanes with epichlorohydrin and then reacting the reaction product with (meth) acrylic acid and/or with hydroxyalkyl and/or hydroxycycloalkyl esters of (meth)acrylic acid; vinyltrialkoxysilanes having 5 to 8 carbon atoms and methacryloyloxypropyltrialkoxysilanes having 10 to 16 carbon atoms.

Particularly preferred further polymerizable comonomers are selected from the group consisting of
a1) non-functional (meth)acrylates, in particular esters of (meth)acrylic acid with alkanols, for example with monohydroxyalkanes having 1 to 14 carbon atoms, such as methyl acrylate, methyl methacrylate, ethyl acrylate, ethyl methacrylate, n-butyl acrylate, n-butyl methacrylate, i-butyl acrylate, i-butyl methacrylate, t-butyl acrylate, t-butyl methacrylate, lauryl acrylate, lauryl methacrylate, 2-ethylhexyl acrylate, 2-ethylhexyl methacrylate, stearyl acrylate, stearyl methacrylate, behenyl acrylate, behenyl methacrylate, cyclohexyl acrylate, cyclohexyl methacrylate, isobornyl acrylate and isobornyl methacrylate; methoxypolyethylene glycol monoacrylate, methoxypolyethylene glycol monomethacrylate,
a2) hydroxyethyl acrylate, hydroxyethyl methacrylate, hydroxypropyl acrylate, hydroxypropyl methacrylate, hydroxyalkyl vinyl ethers such as hydroxybutyl vinyl ether, N,N-dimethylaminoethyl acrylate, N,N-dimethylaminoethyl methacrylate, N,N-dimethylaminopropyl acrylate, N,N-dimethylaminopropyl methacrylate,
a3) acrylic acid and methacrylic acid,
a4) vinyl acetate,
a8) glycidyloxypropyl acrylate, glycidyloxypropyl methacrylate,
a9) styrene, alpha-methylstyrene,
a10) acrylonitrile, methacrylonitrile,
a11) ethyl vinyl ether, n-butyl vinyl ether, cyclohexyl vinyl ether, vinyl acetate,
a13) vinyltriethoxysilane, methacryloyloxypropyltrimethoxysilane,
and mixtures thereof.

Particularly preferred is that at least one further monomer as comonomer is used, which contains an (meth)acrylic group and is selected from the group consisting of methyl (meth)acrylate, ethyl (meth)acrylate, n-butyl (meth) acrylate, i-butyl (meth)acrylate, t-butyl (meth)acrylate, lauryl (meth)acrylate, 2-ethylhexyl (meth)acrylate, stearyl (meth)acrylate, behenyl (meth)acrylate, cyclohexyl (meth) acrylate, isobornyl (meth)acrylate, methoxypolyethylene glycol mono(meth)acrylate, hydroxyethyl (meth)acrylate, hydroxypropyl (meth)acrylate and (meth)acrylic acid, in particular when copolymerized together with a polyether-polysiloxane macromonomer of formula (IV).

In particular, the use of polyethylene glycol mono(meth) acrylates and/or methoxypolyethylene glycol mono(meth) acrylates, may improve the solubility of the copolymers of the invention in water or improve their ability to be emulsifiable in water. Such products are particularly suitable for incorporation of the copolymers into into aqueous compositions, like aqueous coating compositions. Thus, it is preferable to use at least one of the monomers as comonomers for preparing the inventive copolymer.

In order for the coating compositions and polymeric moulding compounds of the invention to retain their high surface energy, hydrophilicity, antifogging properties over a long period of time such as over a plurality of cleaning cycles, it is preferred to fix the inventive copolymer contained therein on the surface of the substrate to be coated via reactive groups such as OH-groups. Such groups can be in particular introduced into the copolymer by use of monomers a2) or a3). Furthermore, monomeric units containing functional groups may be used in order to allow later binding into the respective polymeric matrix or the binder of the compositions. Examples of monomeric units containing functional groups that may be used are in particular acrylonitrile, acrylic acid, methacrylic acid, hydroxyalkyl acrylates or hydroxyalkyl methacrylates of straight-chain, branched or cycloaliphatic diols having from 2 to 36 carbon atoms. The functional comonomers used for the preparation of the inventive copolymers are in particular hydroxy-functional and/or carboxyl-functional, in particular carboxyl-functional. Monomers which can crosslink with reactive groups of the binder ensure long lasting effects with respect to different properties of the resulting crosslinked composition. In order to control crosslinking of the resulting hydroxyl-functional or carboxyl-functional copolymers with, for example, acrylic-melamine-formaldehyde resins, it is also possible to react some or all of these hydroxyl groups with isocyanates to give secondary carbamate groups, such that the crosslinking of the overall system leaves the copolymer enough time to approach the interface, to display its effect there and, after a certain time delay, to react with the melamine-formaldehyde resin. Moreover, it was also found to be particularly advantageous that the hydroxyl groups of the monomer units in the inventive copolymers can crosslink with reactive groups of the binder and thus ensure a permanent effect.

Thus, in order to ensure sufficient compatibility of the copolymers containing polyether/polysiloxane side chains with the coating compositions or polymeric moulding compounds, it is sensible to incorporate reactive groups such as hydroxyl and/or carboxylic acid functionality into the branched polymer. Preference is given to copolymers of the invention having at least one OH-group and an OH number of between 1 and 250 mg KOH/g and an acid number of between 0.5 and 30 mg KOH/g. Preferably, the copolymers have free OH groups. More preferably, the copolymers have an OH number of 5-200 mg KOH/g, very preferably of 10-100 mg KOH/g.

Preferably, at least one OH-functional monomer is used for preparation of the inventive copolymer, especially upon formation of the (meth)acrylic backbone according to the grafting to method. Particularly preferred hydroxyl-functional monomers include: hydroxylalkyl (meth)acrylates of straight-chain diols having 2 to 36 carbon atoms or branched or cycloaliphatic diols having 3 to 36 carbon atoms, for example 2-hydroxyethyl (meth)acrylate, 3-hydroxypropyl (meth)acrylate, 4-hydroxybutyl (meth)acrylate, 3,4-dihydroxybutyl (meth)acrylate, 2-hydroxypropyl (meth)acrylate, 2,5-dimethyl-1,6-hexanediol mono(meth)acrylate, polyethylene glycol mono(meth)acrylate, polypropylene glycol-ethylene glycol mono(meth)acrylate and hydroxyalkyl vinyl ethers, for example hydroxybutyl vinyl ether. Further suitable monomers are caprolactone- and/or valerolactone-modified hydroxyalkyl acrylates and caprolactone- and/or valerolactone-modified hydroxyalkyl methacrylates having a weight-average molecular weight between 220 and 1200 g/mol, the hydroxyl (meth)acrylates preferably being derived from straight-chain diols having 2 to 8 carbon atoms or branched or cycloaliphatic diols having 3 to 8 carbon atoms.

Preferably, at least one COOH functional monomer is used for preparation of the inventive copolymer, especially upon formation of the (meth)acrylic backbone according to the grafting to method. Particularly preferred COOH-functional monomers include: acrylic acid, methacrylic acid, ethacrylic acid, crotonic acid, maleic acid, fumaric acid and itaconic acid, in particular acrylic acid and methacrylic acid.

Preferably, the copolymer is formed to an extent of from 0.1 to 95 wt.-%, more preferably of from 0.5 to 70 wt.-%, even more preferably of from 1.0 to 50 wt.-%, in particular of from 5.0 to 25 wt.-%, based on the total weight of all macromonomers according to formulae (IV) or (IVa) and comonomers used, from polymerized macromonomers according to formulae IV) or (IVa). This content of macromonomers gives the best properties of the inventive copolymers with regard to use as additives in compositions, in particular for improving levelling and the surface-modifying action, for example increasing the surface energy of the coating.

As stated hereinbefore, the inventive copolymer can be prepared by two processes, namely the "macromonomer method" as described hereinbefore (steps (c) and (d)), or by the "grafting to method". The first two steps (a) and (b) as described hereinbefore, are identical for both methods.

"Grafting to Method"

In the "grafting to method" a (meth)acrylic polymer including its (meth)acrylic backbone is formed first and the polyether-polysiloxane side chain or side chains are attached thereto in a polymer analogous reaction, e.g. by transesterification, addition reaction or condensation reaction. Preferably a (meth)acrylic polymer including a (meth)acrylic backbone is formed first by polymerization of at least monomer containing both a (meth)acrylic group such as a (meth)acrylate group and a reactive functional group, and the polyether-polysiloxane side chain or side chains are then attached to the formed (meth)acrylic backbone in a polymer analogous reaction, e.g. by transesterification, addition reaction or condensation reaction, via reaction of said reactive functional group with the functional polyether-polysiloxane macromonomer precursor, preferably with a macromonomer precursor as obtained from step (b), i.e. with a compound of formula (III) ("grafting to" method).

According to the grafting to method method, the inventive copolymer is thus obtainable by radical copolymerization, preferably by free-radical copolymerization, of at least one or more than one radically, preferably free-radically, polymerizable (meth)acrylic monomer(s) to prepare the (meth)acrylic backbone a. of the inventive polymer, wherein at least one of the one or more than one radically, preferably free-radically, polymerizable (meth)acrylic monomer(s) preferably bears a reactive functional group such as an OH- and/or COOH-group in a step (e). The thus obtained (meth)acrylic copolymer bearing at least one reactive functional group such as a OH- and/or COOH-group is then reacted in a polymer analogous reaction in a step (f), e.g. by transesterification, addition reaction or condensation reaction with a suitable, preferably functional component in order to introduce the one or more polysiloxane-polyether side chains into the backbone, preferably with at least one compound of formula (III) as obtained after performing step (b) as described hereinbefore.

Thus, in step (e), the (meth)acrylic backbone of the inventive (meth)acrylic copolymer having a functional reactive side group is prepared in a radical, preferably free-radical, copolymerization and, in a further step (f), a suitable functional polyether-polysiloxane such as at least one compound of formula (III) is reacted with the functional reactive group of the (meth)acrylic backbone to form a covalent bond.

For example, a reactive double bond and an acid function may be incorporated into the copolymer by reacting a (meth)acrylic (co)polymer containing hydroxy-functional monomeric units with maleic anhydride. Further suitable anhydrides for introducing the acid function are, for example, succinic anhydride, phthalic anhydride and trimellitic anhydride, a further possibility being the esterification of hydroxy-functional monomeric units within a copolymer with structurally different anhydrides. It is also possible to esterify free OH groups by, for example, subsequent reaction with acetic anhydride. For better solubility in water, the acid function may also be converted to the salt form using, for example, alkanolamines. Moreover, it is possible by subsequently acrylating and/or methacrylating the hydroxyl group to obtain products which can be incorporated securely into paint systems even in the case of radiation cure processes, such as UV and electron beam curing.

All (meth)acrylic monomers described hereinbefore in connection with the macromonomer method (therein as "comonomers") such as the monomers a1) to a13) can also be used in step (e) of the grafting to method, provided that at least one kind of the monomers are (meth)acrylic monomer(s), which contain a reactive functional group such as a OH- and/or COOH-group.

Examples of suitable carboxy-functional monomers are in particular: acrylic acid, methacrylic acid, maleic acid, fumaric acid and itaconic acid. Further examples of suitable functional monomers are epoxy-functional and silane-functional comonomers such as epoxyalkyl acrylates or epoxyalkyl methacrylates of straight-chain, branched or cycloaliphatic hydroxy epoxides having from 3 to 6 carbon atoms, or else vinyltrialkoxysilanes having from 5 to 8 carbon atoms: the use of epoxy-functional comonomers, for example glycidyl acrylate and glycidyl methacrylate, such as glycidoxy-propyl acrylate or glycidoxypropyl methacrylate, or silane-functional comonomers such as vinyltriethoxysilane and methacryloyloxypropyltrimethoxysilane, can give copolymers which self-crosslink in a controlled manner. Ethylenically unsaturated monomers containing an isocyanate group, as well, such as isocyanatomethyl methacrylate or isopropenylcumyl isocyanate, for example, may also be used. However, as stated hereinbefore, the use of monomers having isocyanate groups is undesired and thus not preferred. Ionic groups can also be introduced into the copolymer as a corresponding ionic, ethylenically unsaturated monomer, or can be obtained subsequently by polymer-analogous reactions, for example salt formation: For example, it is possible to react acid functions in the copolymer, for example carboxylic acids and phosphoric esters, with bases. It is additionally possible, proceeding from acid anhydrides, for example maleic anhydride, first to generate the carboxylic acid function by hydrolysis with water or formation of a monoester or partial ester with monohydric alcohols or polyethers, and then to react this with bases. Oxirane structures in the copolymer can be reacted with nucleophiles such as o-phosphoric acid and then converted to salts with bases to give ionic groups. Hydroxyl functionalities in the copolymer can be reacted with polyphosphoric acid to give phosphoric esters with subsequent conversion to salts with bases to give ionic groups. Suitable bases are, for example, amines, for example dimethylaminoethanol, diethanolamine, triethanolamine, 2-(dimethylamino)propan-1-ol, triethylamine, butylamine and dibutylamine, hydroxides, oxides, carbonates and hydrogencarbonates of metals of main groups 1 to 3 of the Periodic Table of the Elements, for example sodium hydroxide, potassium hydroxide, aluminum hydroxide and sodium hydrogencarbonate. Examples of ionic, ethylenically unsaturated monomers are, for example, salts of acrylic acid, methacrylic acid, maleic acid or styrenesulfonic acid.

The reaction conditions, catalysts and solvents for step (e) of the grafting to method are the same as have already been described above in connection with step (d) according to the macromonomer method. Preference is given to using at least one solvent.

Preference is given to using the functional reactive polyether-polysiloxane such as at least one compound of formula (III) in step (f) of the grafting to method in such an amount that 0.1 to 100% of the functional groups present in the polymerized functional (meth)acrylic backbone are converted. If some functional groups present in the polymerized functional (meth)acrylic backbone are needed for other reactions or for crosslinking in the binder systems, then all of them must not be converted in the reaction with the functional reactive groups of the polyether-polysiloxane moieties of the functional reactive polyether-polysiloxane such as at least one compound of formula (III).

Preferably, the copolymer is formed to an extent of from 0.1 to 95 wt.-%, more preferably of from 0.5 to 70 wt.-%, even more preferably of from 1.0 to 50 wt.-%, in particular of from 5.0 to 25 wt.-%, based on the total weight of all macromonomer precursors according to formula (III) and comonomers used, from macromonomer precursors according to formula (III). This content gives the best properties of the inventive copolymers with regard to use as additives in compositions, in particular for improving levelling and the surface-modifying action, for example increasing the surface energy of the coatings.

Composition

A further subject-matter of the present invention is a composition comprising at least one inventive copolymer in an additive amount, i.e. in relatively small amounts.

All embodiments preferred in connection with the inventive copolymer described hereinabove are also preferred embodiments of the inventive copolymer as a constituent of the composition of the invention.

Preferably, the composition is a coating composition, a moulding compound or a cosmetic formulation.

In case the inventive composition is a moulding compound, said moulding compound is preferably a polymeric moulding compound. Polymeric moulding compounds are understood to preferably encompass thermoset polymeric moulding compounds as well as thermoplastic polymeric moulding compounds. By moulding compounds are meant in the sense of the present inventions compositions which can be processed to mouldings.

Said composition preferably contains said at least one inventive copolymer in an amount of from 0.1 to 10 wt.-%, preferably of from 0.2 to 8 wt.-%, more preferably of from 0.3 to 7 wt.-% or of from 0.3 to 6 wt.-% or of from 0.3 to 5 wt.-%, in particular of from 0.5 to 5.0 wt.-%, based in each case on the total weight of the solids content of the composition.

The inventive copolymers are added preferably as 100% substances, as a solution, as dispersion or as an emulsion.

The properties of the compositions, in particular of the coating compositions, moulding compounds and cosmetic formulations are not impaired by the amount of the inventive copolymer present therein. The presence or use of these copolymers does not have a negative effect e.g. in respect of corrosion protection, gloss preservation, weather resistance and/or mechanical strength of the coatings obtained from these compositions.

If the inventive copolymers contain at least one free reactive group such as an OH-group and/or a carboxyl acid group, it has been found to be particularly advantageous that the reactive groups of the copolymers can crosslink with reactive complementary groups of the binder and thus ensure a permanent effect. In this case the desired hydrophilic properties are generally retained even over a long period of time and even over several cleaning cycles.

The composition of the invention can be an aqueous or solvent-based composition.

The inventive compositions preferably comprise at least one binder. All customary binders known to the skilled person are suitable as binder component of the composition of the invention. The binder used in accordance with the invention preferably has crosslinkable functional groups. Any customary crosslinkable functional group known to the skilled person is contemplated here. More particularly the crosslinkable functional groups are selected from the group consisting of hydroxyl groups, amino groups, carboxylic acid groups, and unsaturated carbon double bonds, isocyanates, polyisocyanates, and epoxides such as ethylene oxides. The binder may be exothermically or endothermically crosslinkable or curable. The binder is crosslinkable or curable preferably in a temperature range from −20° C. up to 250° C.

The binder is preferably selected from the group consisting of epoxide resins, polyesters, wherein the polyesters may be unsaturated, vinyl ester-based resins, poly(meth)acrylates, polyurethanes, polyureas, polyamides, polystyrenes, polyethers including polycarbonates, polyisocyanates, and melamine formaldehyde resins. These polymers may be homopoylmers or copolymers. These resins and their preparation are known to the skilled person.

The composition of the invention can be provided as a one-component system or as a two-component system.

The composition of the invention preferably comprises the binder in an amount of 3 to 90 wt.-%, preferably in an amount of 5 to 80 wt.-%, more preferably in an amount of 10 to 75 wt.-%, based on the total weight of the composition.

Depending on the desired application, the composition of the invention may comprise one or more customarily employed additives as component. These additives are preferably selected from the group consisting of emulsifiers, flow control assistants, solubilizers, defoaming agents, stabilizing agents, preferably heat stabilizers, process stabilizers, and UV and/or light stabilizers, catalysts, waxes, flexibilizers, flame retardants, reactive diluents, adhesion promoters, organic and/or inorganic nanoparticles having a particle size<100 nm, process aids, plasticizers, fillers, glass fibers, reinforcing agents, additional wetting agents and dispersants, light stabilizers, ageing inhibitors and mixtures of the aforesaid additives. Said additive content of the composition of the invention may vary very widely depending on intended use. The content, based on the total weight of the composition of the invention, is preferably 0.1 to 10.0 wt.-%, more preferably 0.1 to 8.0 wt.-%, very preferably 0.1 to 6.0 wt.-%, especially preferably 0.1 to 4.0 wt.-%, and particularly 0.1 to 2.0 wt.-%.

The inventive compositions may be used in pigmented or unpigmented form and may also comprise fillers such as calcium carbonate, aluminium hydroxide, reinforcing fibres such as glass fibres, carbon fibres and aramid fibres.

The coating compositions of the invention are preferably coating compositions for producing anti-static coatings, antifogging coatings, self-cleaning facade coatings, car coatings, dirt-instrument coatings, marine coatings (anti-fouling coatings), and primer coatings. Owing to the outstanding compatibility of the copolymers, they are also outstandingly suitable for producing transparent coatings.

The compositions of the invention may be applied to a large number of substrates, such as wood, paper, glass, ceramic, plaster, concrete and metal, for example. In a multi-coat process the coatings may also be applied to primers, primer-surfacers or basecoats. Curing of the compositions depends on the particular type of crosslinking and may take place within a wide temperature range from, for example, −10° C. to 250° C.

The preferably polymeric moulding compounds of the invention preferably comprise at least one polymer selected from the group consisting of lacquer resins, alkyd resins, polyester resins, epoxy resins, polyurethane resins, unsaturated polyester resins, vinyl ester resins, polyethylene, polypropylene, polyamides, polyethylene terephthlate, PVC, polystyrene, polyacrylonitrile, polybutadiene, polyvinyl chloride or mixtures of these polymers or any copolymers thereof.

Use of the Inventive Copolymers

The invention further provides for the use of the inventive copolymers as additives in compositions such as coating compositions, moulding compounds and cosmetic formulation. Preferably, said composition contains said at least one inventive copolymer in an amount of from 0.1 to 10 wt.-%, preferably of from 0.2 to 8 wt.-%, more preferably of from 0.3 to 7 wt.-% or of from 0.3 to 6 wt.-% or of from 0.3 to 5 wt.-%, in particular of from 0.5 to 5.0 wt.-%, in each case based on the total weight of the solids content of the composition.

The inventive copolymer can be used as additives in compositions, preferably as additives selected from the group consisting of levelling agents, wetting and/or spreading agents, additives to ameliorate overspray acceptance, anti-cratering agents, surface modification agents, emulsifiers, compatibilizers (i.e. compatibility enhancing agents), hydrophilicity increasing agents, antistatic agents, in particular in order to reduce static electricity and/or to reduce the attraction of dust, and anti-fogging agents.

In particular, the inventive copolymers are used as levelling agents, in particular in coating compositions, for example in order to improve the optical properties of the resulting coatings. The use of these copolymers as levelling agents can, for example, also improve the gloss and/or opalescence of the compositions and the coatings resulting therefrom.

The copolymers can also be used, for example, to alter the surface properties of the resulting coatings obtained from the compositions upon application. The addition of the copolymers can increase the surface energy of the resulting coatings. The surface can be made more hydrophilic such that adhesion on this surface is improved, as a result of which it is possible to obtain surfaces such as primers that are easier to overcoat for example with waterborne coatings or easier to recoat with primers. In general, an increase in the surface energy achieves more hydrophilic surfaces which can be wetted more easily and give better adhesion conditions.

In the inventive copolymers, the proportion of hydrophilic groups is preferably dominant compared to the hydrophobic groups. The copolymer in this case has a hydrophilic character overall. In these copolymers, the effect of relatively small amounts of polysiloxane groups is to favour the orientation of the copolymer to the coatings' surface/air interface and therefore the segregation of the copolymers to the surface, where the dominant proportion of hydrophilic groups can then lead to an increase in surface energy. Copolymers suitable for increasing the surface energy accordingly contain, in addition to the polysiloxane groups present, comparatively hydrophilic groups, i.e. polyether units, by using (meth)acrylic monomers bearing such polyether units for the preparation thereof or by virtue of a significant polyether content in the polyether-polysiloxane side chain and in the copolymer.

Coatings obtained from any of the inventive compositions to which at least one of the inventive copolymers is added have surfaces of excellent wettability. Wettability can be determined by determining the contact angle of the surface with respect to water by customary methods. For hydrophilic surfaces, the contact angle should be <60°. Correspondingly, surfaces coated with any of the inventive compositions, have a very good wettability and can even exhibit adhesion-promoting properties in the case of overpainting.

The use of the copolymers as additives in the inventive compositions can also give surfaces having antistatic properties, low dirt pick-up, or antifogging properties.

Test Methods

Determination of $M_n$ and $M_w$

The number average ($M_n$) and weight average ($M_w$) molecular weights and the molecular weight distribution of the prepared macromonomers and copolymers or any precursors thereof are determined by GPC-analysis (gel permeation chromatography analysis) according to DIN 55672-1:2007-08 at 40° C. using a high-pressure liquid chromatography pump (WATERS 600 HPLC pump) and a refractive index detector (Waters 410). A combination of 3 Styragel columns from WATERS with a size of 300 mm×7.8 mm ID/column, a particle size of 5 µm and pore sizes HR4, HR2 and HR1 is used as separating columns. The eluent used for the copolymers was Tetrahydrofuran with 1% by volume of Dibutylamine with an elution rate of 1 ml/min. The conventional calibration was carried out using Polystyrene standards. For the macromonomers and all macromonomer precursors the eluent was Toluene with an elution rate of 1 ml/min. The conventional calibration was carried out using Polydimethylsiloxane standards.

Iodine Number

The equivalent weight average of SiH-functional PDMS macromonomer precursors such as of the SiH-functional PDMS macromonomers SM1 to SM4 disclosed in the experimental part and the SiH-conversion during the Hydrosilylation reaction for the preparation of the macromonomer precursors such as the PDMS-Polyether block-copolymers SM1PE1, SM1PE2, SM2PE1, SM2PE2, HTM-SPE2 (all inventively used) as well as for component HTMS-OH (comparatively used) is determined according to DIN 53241-1 via volumetric measurement of $H_2$.

OH Number

The equivalent weight average of OH-functional PDMS-Polyether block-copolymers and the OH-conversion during the trans-esterification reaction for the preparation of PDMS-Polyether block-macromonomers is determined according to DIN ISO 4629.

Solid Matter

The amount of solid matter is determined via DIN EN ISO 3251:2008-06 at 150° C. for 20 min.

Examples

The following examples further illustrate the invention but are not to be construed as limiting its scope. In the following, all amounts given in the Tables are parts by weight if not indicated otherwise.

| Raw materials: | |
|---|---|
| THF | Tetrahydrofuran (Aldrich) |
| Breox AA E 550H | Allyl polyethylene glycol, 550 g/mol iodine number 46.1 g $I_2$/g (manufacturer: BASF) |
| Uniox PKA5002 | Allyl polyethylene glycol, 450 g/mol, iodine number 64.7 g $I_2$/g (manufacturer: NOF) |
| Allylalcohol | iodine number 576.8 g J/g, (Aldrich) |
| Bisomer MPEG550MA | methoxy polyethylene glycol 550 methacrylate (manufacturer: Cognis/BASF) |
| MMA | methyl methacrylate (manufacturer: Evonik) |
| EHA | 2-ethylhexyl acrylate (manufacturer: Evonik) |
| Trigonox 21 | tert-butyl peroxy-2-ethylhexanoate (manufacturer: Akzo Nobel) |
| Silaplane FM-0721 | mono-methacryl functional Polydimethylsiloxane 5000 g/mol (manufacturer: Chisso) |
| Silaplane FM-0711 | mono-methacryl functional Polydimethylsiloxane 1000 g/mol (manufacturer: Chisso) |
| HMTS | Heptamethyltrisiloxan (Aldrich) |
| AMBN | 2,2'-azodi(2-methylbutyronitrile) (manufacturer: Akzo Nobel) |
| AIBN | 2,2'-azobisisobutyronitrile (manufacturer: Merck) |
| PMA | 1-methoxy-2-propyl acetate (manufacturer: DOW Chemical) |
| Shellsol A | Mixture of aromatics, boiling range 148.9-182.2° C. (manufacturer: Royal Dutch Shell) |
| Bayferrox 303T | Iron oxide-based black pigment (manufacturer: Lanxess) |
| Blanc fixe micro | Organically coated Barium sulfate pigment (manufacturer: Sachtleben) |
| Micro Talc IT extra | Talcum (manufacturer: Mondo Minerals) |
| Aerosil R 972 | Hydrophobic fumed silica (manufacturer: Evonik) |
| Kronos 2310 | Titanium dioxide pigment (manufacturer: Kronos) |
| Bayhydrol E 270 (70%) | Water thinnable, oil-free, saturated polyester, approximately 70 wt.-% in water/butyl diglycol and neutralized with dimethyl ethanol amine (manufacturer: Bayer Material Science) |
| DMEA (10% in Wasser): | N,N-Dimethyl ethanol amine |
| Maprenal MF 904 | Modified melamine formaldehyde resin (manufacturer: INEOS) |
| Maprenal MF 915 | Modified melamine-formaldehyde resin (manufacturer: INEOS) |
| Bayhytherm 3246 (46%) | Water-borne, self-crosslinking PU resin for stoving systems (manufacturer: Bayer Material Science) |
| Setalux 1756 VV - 65 | Thermosetting acrylic resin in Solvent Naphtha (manufacturer: Nuplex) |
| Setamine US 138 BB-70 | Partly butylated melamine in n-butanol (manufacturer: Nuplex) |
| Bayhydrol A 145 | Hydroxy-Functional Polyacrylic Dispersion (manufacturer: Bayer Material Science) |
| Bayhydrol UH 2621 | Aliphatic polyurethane resin dispersion for waterborne, highly stone-chip resistant coatings (manufacturer: Bayer Material Science) |
| Bayhydrol U 241 | PES/PUR dispersion (manufacturer: Bayer Material Science) |
| Viscalex HV 30 | Thickener, acrylic copolymer emulsion in water (manufacturer: BASF) |
| Cymel 328 | Crosslinker, high solids, methylated melamine-formaldehyde resin (manufacturer: Allnex) |
| Setalux 6100 GR-68 | Thermosettling acrylic resin in dibutyl glycol (manufacturer: Nuplex) |
| Setaqua 6160 | Thermosettling acrylic resin in water/butyl glycol (manufacturer: Nuplex) |
| Luwipal 072 | highly reactive melamine-formaldehyde resin (manufacturer: BASF) |

-continued

| Raw materials: | |
|---|---|
| Disperbyk-180 | Wetting and Dispersing additive, (manufacturer: BYK) |
| BYK-346 | Silicone-based substrate wetting additive, (manufacturer: BYK) |
| BYK-1710 | Defoamer additive, (manufacturer: BYK) |
| BYK-349 | Silicone-based substrate wetting additive, (manufacturer: BYK) |
| BYK-011 | Defoamer additive, (manufacturer: BYK) |
| BYK-3560 | Leveling additive, silicone-free surface additive for increasing the surface energy in aqueous, solvent-borne, UV-curable, and high-solid systems, (manufacturer: BYK) |
| BYK-Silclean 3700 | Silicone-containing surface additive for solvent-borne coating systems to improve the easy-to-clean effect by decreasing the surface energy, (manufacturer: BYK) |

General Procedure for the Preparation of SiH-Functional Polydimethylsiloxane (PDMS) Macromonomer Precursors SM1 and SM2

A four-necked flask provided with stirrer, thermometer, dropping funnel and nitrogen inlet tube is heated carefully to 150° C. under nitrogen flow using a heat gun to remove traces of water. After cooling of the apparatus to ambient temperature under nitrogen flow, the vessel is charged with a solution Hexamethylcyclotrisiloxane (D3) in Cyclohexane, which has been dried over molecular sieve A3 for 24 h. At a reaction temperature of 20° C., the Butyllithium solution (1.7M in hexane) was introduced over a period of 5 min. The reaction mixture was not allowed to exceed 30° C. by cooling with a water bath. After 30 min, THF was slowly added to start the polymerization reaction. The temperature was monitored and kept below 30° C. After 5 h, the reaction was quenched by the addition of Dimethylchlorosilane and stirred for additional 30 min. Afterwards, the mixture was neutralized by the addition of a Sodium bicarbonate solution in water (8.0 wt.-%) and vigorously stirred for 1 h. The organic layer was separated, distilled in vacuum (20 mbar at 100° C.) to remove all solvents completely and filtered through a plug of Celite. The product (unsymmetrical, SiH-functional Polydimethylsiloxane) is a clear, colorless liquid of low viscosity.

TABLE 1

Raw materials for the preparation of SiH-functional PDMS precursors SM1 and SM2

| | SiH-functional PDMS macromonomer precursors | |
|---|---|---|
| Raw materials in g | SM1 | SM2 |
| D3 [g] | 114.3 | 88.3 |
| Cyclohexane [g] | 91.8 | 70.9 |
| Butyllithium solution (1.7M in hexane) [g] | 79.3 | 27.6 |
| THF [g] | 91.8 | 70.9 |
| Dimethylchlorosilane [g] | 29.9 | 10.9 |
| Sodium bicarbonate solution (8 wt.-% in water) [g] | 32.9 | 16.0 |
| analytical data | | |
| Iodine number | 45.4 | 26.2 |
| $M_n$ | 508 | 955 |
| $M_w/M_n$ | 1.07 | 1.23 |

SM1 and SM2 are inventively used precursors.

General Procedure for the Preparation of OH-Functional Polydimethylsiloxane-Polyether Block-Copolymers (Macromonomer Precursors) SM1 PE1, SM1 PE2, SM2PE1, SM2PE2, HTMSPE2 (all Inventively Used) as Well as for Component HTMS-OH (Comparatively Used)

A four-necked flask provided with stirrer, thermometer, dropping funnel and nitrogen inlet tube is charged with the allyl-functional polyether, which is used in an molar excess of 30% with respect to the Hydrosilylation reaction, 10% of the amount of the SiH-functional PDMS macromonomer and 60 mg 2,6-Di-tert-butyl-4-methylphenol. The components are mixed thoroughly and nitrogen is passed over the mixture throughout the reaction. After the reaction temperature has been increased to 75° C., 0.66 g catalyst (2 wt.-% Karstedt's catalyst in Xylene) are charged and subsequently the remaining 90% of the amount of the SiH-functional PDMS macromonomer are metered into the vessel. The reaction temperature is observed closely and held below 130° C., if necessary by stopping the macromonomer addition and cooling with a water bath. After the end of charging the reaction temperature is maintained at 115° C. for 60 minutes and the conversion of SiH was monitored via Iodine number. After complete consumption of all SiH functions, the reaction mixture was cooled to ambient temperature and filtered through a cellulose filter paper (5-13 μm). The product (OH-functional Polyether-PDMS block-copolymer (macromonomer precursor)) is clear, slightly yellow and slightly viscous.

sieve A3 for 24 h. At a reaction temperature of 20° C., 196.0 g Butyllithium solution (1.7M in hexane, Aldrich) was introduced over a period of 5 min. The reaction mixture was not allowed to exceed 30° C. by cooling with a water bath. After 30 min, 218.5 g THF was slowly added to start the polymerization reaction. The temperature was monitored and kept below 30° C. After 5 h, the reaction was quenched by the addition of 180.9 g Methacryloxypropyldimethylchlorosilane (97%, ABCR) and stirred for additional 30 min. Afterwards, the mixture was neutralized by the addition of a 9.5 g Sodium bicarbonate solution in 105.0 g water (8.0 wt.-%) and vigorously stirred for 1 h. The organic layer was separated, distilled in vacuum (20 mbar at 100° C.) to remove all solvents completely and filtered through a plug of Celite. The product (unsymmetrical, methacryl-functional Polydimethylsiloxane) is a clear, colorless liquid of low viscosity.

SM1MA is a comparatively used macromonomer since it lacks polyether moieties.

General Procedure I for the Preparation of Methacryl-Functional (MA) Polydimethylsiloxane-Polyether Macromonomers A four-necked flask provided with stirrer, thermometer and air inlet tube is charged with PDMS-Polyether block-copolymer macromonomer precursors (e.g. SM1PE1 as per table 3), MMA and 125 mg 4-Methoxyphenol. The components are mixed thoroughly and a minimal amount of air (~10 L/hour) is bubbled into the mixture to prevent MMA

TABLE 2

Raw materials and analytical data for the preparation of PDMS-Polyether block-copolymers

| Raw materials in g | OH-functional PDMS-Polyether (PE) block-copolymers | | | | | |
| --- | --- | --- | --- | --- | --- | --- |
| | SM1PE1 | SM2PE1 | SM1PE2 | SM2PE2 | HMTS-PE2 | HMTS-OH |
| SM1 | 129.4 | | 120.2 | | | |
| SM2 | | 125.8 | | 122.5 | | |
| HMTS | | | | | 100.0 | 100.0 |
| Uniox PKA 5002 | 117.3 | 62.2 | | | | |
| Uniox A550 | | | 159.5 | 85.0 | 275.0 | |
| Allyl alcohol | | | | | | 202.5 |
| analytical data | | | | | | |
| OH number (4004) | 69.0 | 48.3 | 61.7 | 42.5 | 79.3 | 186.0 |
| Iodine number (5004) | 0.0 | 0.0 | 0.1 | 0.1 | 0.0 | 0.0 |
| $M_n$ | 572 | 1096 | 642 | 1251 | 461 | 225 |
| $M_w/M_n$ | 1.30 | 1.26 | 1.28 | 1.36 | 1.23 | 1.04 |

Preparation of Methacryl-Functional Polydimethylsiloxane Macromonomer SM1MA (Comparatively Used Macromonomer)

A four-necked flask provided with stirrer, thermometer, dropping funnel and nitrogen inlet tube is heated carefully to 150° C. under nitrogen flow using a heat gun to remove traces of water. After cooling of the apparatus to ambient temperature under nitrogen flow, the vessel is charged with a solution of 272.2 g Hexamethylcyclotrisiloxane (D3) in 218.5 g Cyclohexane, which has been dried over molecular polymerization. After the reaction temperature has been increased to 65° C., 0.43 g Zirconium-2,4-pentanedionate is charged and the reaction temperature is raised to 110° C. and maintained for 420 minutes. Afterwards, the excessive methyl methacrylate is removed completely by distillation under vacuum on a rotary evaporator (25 mbar, gentle air stream via inlet tube, 100° C.). The solid contend is >98%. The product (methacrylated PDMS-Polyether macromonomer) is clear, yellow and slightly viscous.

TABLE 3

Raw material amounts and analytical data for the synthesis of
PDMS-polyether macromonomers according to General procedure I

| Raw materials in g | PDMS-Polyether Macromonomers | | | | | |
|---|---|---|---|---|---|---|
| | SM1PE1-MA | SM1PE2-MA | SM2PE1-MA | SM2PE2-MA | HMTSPE2-MA | HMTS-O-MA |
| SM1PE1 | 150.0 | | | | | |
| SM1PE2 | | 150.0 | | | | |
| SM2PE1 | | | 150.0 | | | |
| SM2PE2 | | | | 150.0 | | |
| HTMSPE2 | | | | | 150.0 | |
| HTMS-OH | | | | | | 150.0 |
| MMA | 130.0 | 70.0 | 125.0 | 67.0 | 135.0 | 270.0 |
| analytical data | | | | | | |
| OH number | <1.0 | 2.1 | 1.6 | 3.6 | 2.0 | <1.0 |
| Iodine number | 33.4 | 28.6 | 21.2 | 19.7 | 46.8 | 85.1 |
| Solid Matter wt.-% | 98.1 | 97.6 | 98.0 | 97.3 | 97.1 | 97.2 |
| $M_n$ | 876 | 836 | 1410 | 1535 | 619 | 337 |
| $M_w/M_n$ | 1.13 | 1.28 | 1.25 | 1.29 | 1.15 | 1.06 |

HTMS-O-MA is a comparatively used macromonomer since it lacks polyether moieties.

General Procedure II for the Preparation of Methacryl-Functional (MA) Polydimethylsiloxane-Polyether Macromonomers Via a Hydrosilylation Method A four-necked flask provided with stirrer, thermometer, dropping funnel and nitrogen inlet tube is charged with 95.0 g toluene, 30 mg 2,6-Di-tert-butyl-4-methylphenol and with 60.0 g of a SiH-functional PDMS macromonomer precursor SM1 (iodine number of 45.4). The components are mixed thoroughly and nitrogen is passed over the mixture throughout the reaction. After the reaction temperature has been increased to 60° C., 1.9 g catalyst (1 wt.-% Karstedt's catalyst in Xylene) are charged and subsequently an amount of 74.8 g of an alpha (methacryloxypropyl) omega-(allyloxy) polyethylene glycol with an average of 9.5 ethylene oxide repeating units and an iodine number of 44.8) are metered into the vessel. The reaction temperature is observed and held below 90° C., if necessary by stopping the allyl/methacryl PEG addition and cooling with a water bath. After the end of charging the reaction temperature is maintained at 90° C. and the conversion of SiH was monitored via Iodine number. After complete consumption of all SiH functions, the reaction mixture was cooled to ambient temperature, i.e. 18-23° C. and filtered through a cellulose filter paper (5-13 μm). The product (methacryl-functional Polyether-PDMS block-copolymer (macromonomer)) is clear, slightly yellow and slightly viscous. The number average molecular weight of said macromonomer is 1016 and the polydispersity was determined to be 1.10.

Preparation of the Inventive Copolymers A1 to A5 and Comparative Copolymers B1* to B5*

In a beaker, the monomer mixture as per table 4, including the initial amount of radical initiator Trigonox 21, is prepared and diluted with 20 g Isobutanol. This monomer mixture is transferred into a dropping funnel. A four-necked flask provided with stirrer, thermometer and a nitrogen inlet tube is charged with Isobutanol as per table 4 and heated to 110° C. The dropping funnel with the monomer mixture is mounted on the reaction vessel and nitrogen is passed through the reaction apparatus for 10 min. After the reaction temperature is reached the monomer mixture is slowly metered in over a period of 90 min. Thereafter, the reaction temperature is maintained at 110° C. for 30 minutes, before three times 0.1 g Trigonox 21 was added at 30 minute intervals for post-initiation. After the last post-initiation step, the reaction temperature is maintained at 110° C. for another 30 minutes, before the solvent used is removed completely by distillation under vacuum on a rotary evaporator (20 mbar, 120° C.). The copolymers A1 to A5 are liquids, i.e. are present in a liquid state.

TABLE 4

Raw material amounts and analytical data for the synthesis of inventive double-comb-block copolymers A1 to A5 and comparative copolymers B1* to B5*

| Raw materials in g | Monomer mixture | | | | | | | | | |
|---|---|---|---|---|---|---|---|---|---|---|
| | A1 | A2 | A3 | A4 | A5 | B1* | B2* | B3* | B4* | B5* |
| Isobutanol | 60 | 60 | 60 | 60 | 60 | 60 | 60 | 60 | 60 | 60 |
| SM1PE1MA | | 6.7 | | | | | | | | |
| SM1PE2MA | 16.6 | | | | | | | | | |
| SM2PE2MA | | | 16.6 | 6.7 | | | | | | |
| HMTSPE2MA | | | | | 12.9 | | | | | |
| SM1MA | | | | | | 12.9 | 51.7 | | | |
| Silaplane FM-0711 | | | | | | | | 12.9 | 51.7 | |
| HMTS-OMA | | | | | | | | | | 12.9 |
| EHA | 31.4 | 31.4 | 31.4 | 31.4 | 24.3 | 24.3 | 24.3 | 24.3 | 24.3 | 24.3 |
| MPEG550MA | 50.2 | 60.0 | 50.2 | 60.0 | 38.8 | 38.8 | | 38.8 | | 38.8 |
| Trigonox 21 | 1.6 | 1.6 | 1.6 | 1.6 | 1.2 | 1.2 | 1.2 | 1.2 | 1.2 | 1.2 |

TABLE 4-continued

Raw material amounts and analytical data for the synthesis of inventive double-comb-block copolymers A1 to A5 and comparative copolymers B1* to B5*

| Raw materials in g | Monomer mixture | | | | | | | | | |
|---|---|---|---|---|---|---|---|---|---|---|
| | A1 | A2 | A3 | A4 | A5 | B1* | B2* | B3* | B4* | B5* |
| Analytical data | | | | | | | | | | |
| Solid Matter [wt.-%] | 97.8 | 98.1 | 98.0 | 97.3 | 97.1 | 99.4 | 98.8 | 99.7 | 99.4 | 98.1 |
| $M_n$ | 5489 | 5751 | 6601 | 6415 | 5804 | 6276 | 5515 | 8912 | 5734 | 10929 |
| $M_w/M_n$ | 2.56 | 2.49 | 2.79 | 2.67 | 2.77 | 2.83 | 2.21 | 3.47 | 2.00 | 9.79 |

Application and Performance
Preparation of the Water-Borne Primer WP1

The preparation of the water-borne primer and the evaluation of the performance of the surface inventive additives A1 to A5 is separated into several steps for better clarity. The steps are:
1. Preparation of a millbase
2. Preparation of the letdown
3. Adjustment of viscosity for spray application
4. Application, curing and evaluation of the inventive double comp block-Copolymers in WP1
5. Evaluation of leveling of WP1 and wetting of WP1 with a water-borne basecoat.

1. Preparation of the Millbase for the Water-Borne Primer Surfacer WP1

TABLE 5

Raw materials for the preparation of the millbase for the water-borne primer surfacer

| Raw materials | Amount in g |
|---|---|
| Bayhydrol E 270 (70%) | 42.8 |
| demineralized water | 153.2 |
| DMEA (10% in water) | 6.1 |
| BYK-011 | 10.0 |
| DISPERBYK-180 | 7.3 |
| Aerosil R 972 | 3.8 |
| Kronos 2310 | 111.0 |
| Blanc fixe micro | 109.5 |
| Micro Talc IT extra | 27.0 |
| Bayferrox 303T | 1.2 |
| Sum | 471.9 |

All components as per Table 5 are separately loaded in a PE bucket. Afterwards, the millbase was homogenized using a Dispermat SL at 3000 rpm for 30 min. The milling chamber was filled by 80% with Zirconox beads (1.2-1.7 mm)

2. Preparation of the Letdown for the Water-Borne Primer Surfacer WP1

TABLE 6

Raw materials for the preparation of the letdown for the water-borne primer surfacer

| Raw materials | Amounts in g |
|---|---|
| Millbase | 47.19 |
| Bayhydrol E 270 (70%) | 6.38 |
| Maprenal MF 904 | 1.92 |
| Maprenal MF 915 | 2.48 |
| Butyldiglykol | 1.99 |
| Tripropylenglykol | 1.99 |
| BYK-346 | 0.50 |

TABLE 6-continued

Raw materials for the preparation of the letdown for the water-borne primer surfacer

| Raw materials | Amounts in g |
|---|---|
| Bayhytherm 3246 (46%) | 29.66 |
| demineralized water | 7.69 |
| DMEA | 0.20 |
| Sum | 100.0 |
| pH value | 8.3 |
| Surface additive as per table 4 | 0.5 wt.-% and 2.0 wt.-%, respectively, based on total formulation |

The required amount of millbase is loaded in a PE beaker. All components as per table 6 are separately loaded and subsequently stirred using a Dispermat CV equipped with a dissolver disc 50 mm. Afterwards, 0.5% wt.-% and 2.0 wt.-%, respectively, of the inventive or comparative surface additive, respectively, calculated on total formulation (millbase+letdown) was added and stirred for additional 2 min at 3000 rpm. The water-borne primer surfacer was aged overnight at room temperature.

3. Adjustment of Viscosity for Spray Application of Water-Borne Primer Surfacer WP1

The viscosity of the aged letdown containing 0.5 wt.-% of surface additives was adjusted with a 4 mm flow cup to 40 s at 20° C. by the addition of 3-3.5% wt of water.

4. Application, Curing and Evaluation of the Inventive Double Comp Block-Copolymers in a Water-Borne Primer Surfacer WP1

The water-borne primer surfacer WP1 modified with 0.5 wt.-% of the surface additive was applied by means of vertical electrostatic spray application on a cathodic-electro-deposition-primered (CED) panel, 30 cm×50 cm. The curing procedure was carried out vertically with 10 min drying at ambient temperature, 10 min at 80° C. and 20 min at 160° C. stoving. A dry film thickness of 30-40 μm was achieved. The contact angle of water was determined on the coated and cured panels using a Krüss G2 instrument. A contact angle of 90° and higher is considered to be caused by a hydrophobic surface, which is not intended. In contrast, a low contact angle of water (e.g. 35°) expresses the inventive feature of an exceptionally high hydrophilicity of the surface.

TABLE 7

Contact angle of water on the water-borne primer surfacer WP1

| Surface additive 0.5 wt.-% dosage | Contact angle of water in ° |
|---|---|
| Control (without additive) | 82 |
| BYK 3560* | 44 |
| BYK Silclean 3700* | 86 |
| B1* | 51 |
| B2* | 93 |
| B3* | 40 |
| B4* | 94 |
| B5* | 73 |
| A1 | 21 |
| A2 | 29 |
| A4 | 33 |
| A5 | 21 |

Comparative examples are marked with an asterix*

5. Evaluation of the Leveling and Overcoatability of the Inventive Double Comb Block-Copolymers A1 to A5 in the Water-Borne Primer Surfacer WP1 with a Water-Borne Basecoat The water-borne primer surfacer was applied by wire bar application (100 μm wet film thickness) on a primered CED panel 30 cm×50 cm. The curing procedure was carried out vertically with 10 min drying at ambient temperature, 10 min at 80° C. and 20 min at 160° C. stoving. The leveling was measured by determining the surface topography within an area of 2 mm×20 mm with a confocal microscope Microspy Topo DT, FRT GmbH, lens 10×0.2. The value sWt expresses the mean value between the highest peak and the deepest valley within the area of measurement. A low sWt is indicating low waviness and good leveling.

The contact angles of the water-borne basecoat were determined with a Krüss G2 instrument of 50 μL drops of basecoat after 3 seconds. A lower contact angle indicates better wetting of the basecoat WB1 on the water-borne primer surfacer.

Formulation and Preparation of the Water-Borne Basecoat WB1 for the Determination of Wetting Properties on WP1

TABLE 8

Raw materials for the preparation of the water-borne basecoat WB1

| Raw materials | Amounts in g |
|---|---|
| Millbase of WB1 | |
| Demineralized water | 20.1 |
| Disperbyk-190 (40% wt) | 8.8 |
| BYK-011 | 1.0 |
| Acticide MBS | 0.1 |
| Kronos 2310 | 70.0 |
| Clear basecoat formulation for WB1 | |
| Setaqua 6801 AQ 24 | 23.8 |
| Setaqua 6802 AQ 24 | 44.9 |
| BYK-028 | 0.6 |
| DMEA 10% in water | 3.2 |
| Demineralized water | 12.3 |
| Butylglykol | 5.7 |
| BYK-348 | 0.5 |
| BYK-425, 5% wt in water | 9.0 |
| pH value | 8.3 |
| Let down formulation of WB1 | |
| clear basecoat | 59.4 |
| millbase | 17.1 |
| water dem. | 23.5 |
| Pigment content | 12.0 wt.-% |

All components of the millbase are separately loaded in a PE beaker. Afterwards, the millbase was homogenized using a Dispermat CV at 10.000 rpm for 30 min. Per 100 g of formulation, 100 g glass beads 0.6-0.8 mm were used for grinding. All components of the clear basecoat are separately loaded in a PE beaker and homogenized using a Dispermat CV at 3.000 rpm. The pH value was adjusted by the addition of DMEA 10% in water to 8.3.

For the formulation of the letdown of WB1, the letdown components as per table 8 were subsequently combined in a PE beaker under stirring and stirred for additional 2 min at 3000 rpm, afterwards.

TABLE 9

Waviness of the water-borne primer surfacer WP1 and contact angle of a water-borne basecoat WB1

| Surface additive 2.0 wt.-% dosage | Waviness sWt of primer WP1 | Contact angle of basecoat WB1 in° |
|---|---|---|
| Control (without additive) | 2.399 | 45 |
| BYK 3560* | 3.188 | 35 |
| BYK Silclean 3700* | 2.263 | 51 |
| B1* | 3.674 | 35 |
| B2* | 2.618 | 44 |
| B3* | 3.061 | 35 |
| B4* | 3.058 | 43 |
| A1 | 1.749 | 36 |
| A2 | 1.913 | 32 |
| A4 | 1.248 | 37 |
| A5 | 1.444 | 34 |

Comparative examples are marked with an asterix*

Preparation of a Solvent-Borne Clearcoat SC1

The preparation of the solvent-borne clear coat is separated into several steps for better clarity. The steps are:

1. Preparation of the liquid formulation
2. Application, curing and evaluation of the inventive double comp block-copolymers 1. Preparation of the Liquid Formulation of a Solvent-Borne Clear Coat SC1

TABLE 10

Raw materials for the solvent-borne clear coat

| Raw materials | Amount in g |
|---|---|
| Setalux 1756 VV - 65 | 60.0 |
| Setamine US 138 BB-70 | 24.0 |
| Shellsol A | 8.0 |
| Xylene | 8.0 |
| Surface additives as per table | 0.5 wt.-% and 2.0 wt.-%, respectively, based on total weight of the formulation |

All components as per table 10 are separately loaded and subsequently stirred in a PE beaker using a Dispermat CV equipped with a dissolver disc 50 mm at 3000 rpm for 20 min. After aging of the formulation overnight at room temperature, the inventive surface additives and comparative examples as per table 4, were added. Two concentrations (0.5 wt.-% and 2.0 wt.-% based on the total weight of the formulation) of the surface additives were evaluated.

2. Application, Curing and Evaluation of the Inventive Double Comp Block-Copolymers in a Solvent-Borne Clear Coat SC1

The modified clear coat formulation was applied on primered Aluminum panels using a wire bar (100 μm wet film thickness). Afterwards, the panels were dried for 15 min at ambient temperature and then cured for 25 min at 140° C. in a stoving oven. The contact angle of water was determined on the coated and cured panels using a Krüss G2 instrument. Again, a low contact angle of water (e.g. lower than 30°) and a good leveling is desired. The leveling is determined with a BYK wave scan dual instrument indicating LW (long wave) and SW (short wave). Both parameters are intended to be low. In addition, the absence of craters in this application is crucial.

TABLE 11

Contact angle of water and leveling performance in a solvent-borne clear coat SC1

| Surface additive | Contact angle of water in ° | | Leveling | | | | | |
|---|---|---|---|---|---|---|---|---|
| | | | SW | LW | Crater | SW | LW | Crater |
| Control (without additive) | 87 | | 87 | 21.9 | 4.1 | Many | 21.9 | 4.1 | many |
| | 0.5% wt | 2.0% wt | 0.5% wt | | | 2.0% wt | | |
| BYK 3560* | 78 | 29 | 19.1 | 3.5 | few | 20.5 | 2.6 | many |
| BYK Silclean 3700* | 103 | 105 | 22.6 | 1.7 | no | 23.7 | 2.2 | no |
| B1* | 70 | 22 | 26.5 | 1.5 | few | 24.4 | 1.7 | no |
| B2* | 96 | 97 | 55.6 | 21.0 | few | 46.1 | 15.0 | no |
| B3* | 59 | 34 | 35.7 | 8.3 | few | 25.6 | 3.0 | no |
| B4* | 95 | 96 | 64.2 | 36.0 | many | 21.4 | 3.9 | many |
| B5* | 75 | 24 | 25.7 | 1.8 | many | too many craters, no data available | | |
| A1 | 62 | 18 | 22.5 | 1.2 | no | 21.6 | 1.2 | no |
| A2 | 65 | 15 | 27.2 | 2.2 | no | 25.2 | 1.3 | no |
| A3 | 37 | 26 | 26.0 | 1.4 | no | 26.0 | 1.5 | no |
| A4 | 58 | 21 | 26.3 | 1.3 | no | 23.6 | 1.2 | no |
| A5 | 66 | 29 | 22.0 | 2.2 | no | 22.1 | 2.0 | no |

Comparative examples are marked with an asterix*

Preparation of a Water-Borne Top Coat WT1

The preparation of the water-borne top coat is separated into several steps for better clarity. The steps are:
1. Preparation of a millbase
2. Preparation of the letdown
3. Adjustment of viscosity for spray application
4. Application, curing and evaluation of the inventive double comp block-copolymers 1. Preparation of the Millbase of a Water-Borne Top Coat WT1

TABLE 12 raw materials for the preparation of the millbase for the water-borne top coat

| Raw materials | Amount in g |
|---|---|
| Setalux 6100 GR-68 | 82.2 |
| DMEA | 1.6 |
| Butyldiglycol | 27.3 |
| BYK-1710 | 6.0 |
| Disperbyk-180 | 3.3 |
| Kronos 2310 | 164.4 |
| Demineralized water | 30.0 |

All components as per table 12 are separately loaded in a PE bucket. Afterwards, the millbase was homogenized using a Dispermat SL at 1000 rpm for 20 min. The milling chamber was filled to 80% with Zirconox beads (1.2-1.7 mm). The millbase formulation was aged overnight at room temperature.

2. Preparation of the Letdown for a Water-Borne Top Coat WT1

TABLE 13

Raw materials for the preparation of the letdown

| Raw materials | Amounts in g |
|---|---|
| Millbase | 31.48 |
| Setaqua 6160 | 42.38 |
| Luwipal 072 | 10.96 |
| Butyldiglycolacetat | 1.15 |

TABLE 13-continued

Raw materials for the preparation of the letdown

| Raw materials | Amounts in g |
|---|---|
| n-Butanol | 2.00 |
| BYK-349 | 0.10 |
| Deionized Water | 8.93 |
| DMEA (10 wt.-% in water) | 3.00 |
| sum | 100.0 |
| pH value | 8.3 |
| Surface additives as per table 4 | 0.1 wt.-% and 0.3 wt.-%, respectively, based on total weight of formulation |

The required amount of millbase is loaded in a PE beaker. All components as per table 13 are separately loaded and subsequently stirred using a Dispermat CV equipped with a tooth plate (4 cm diameter). Afterwards, the inventive or comparative surface additive, respectively, as per table 4 was added to the letdown formulation and stirred for additional 2 min at 2000 rpm.

3. Adjustment of Viscosity for Spray Application of WT1

The viscosity for the letdown of the water-borne top coat was adjusted with a 4 mm (DIN4) flow cup to 60 s at 20° C.

by the addition of 4.1 wt.-% of water. Afterwards, the letdown formulation was aged overnight at room temperature.

4. Application, Curing and Evaluation of the Inventive Double Comp Block-Copolymers in the Water-Borne Top Coat WT1

The water-borne top coat was applied by means of vertical electrostatic spray application on a primered coil panel 30 cm×50 cm. The curing procedure was carried out vertically with 10 min drying at ambient temperature, 10 min at 80° C. and 20 min at 140° C. stoving. A dry film thickness of 30-40 μm was achieved. The contact angle of water was determined on the coated and cured panels using a Krüss G2 instrument. For the measurement, five different test liquids with well-known surface tension and polar and disperse parts were used. The test liquids are water, Glycerin, Ethyleneglycol, 1-Octanol, n-Dodecane. The contact angle of the test liquids on the coated panels is measured by the advanced contact angle method from drop volumes of 5 to 11 μL. The surface energy is determined with the method of Owens-Wendt-Rabel and Kaelble.

The coefficient of friction was determined by measuring the force, which is needed for moving a weight of 500 g placed on a round platelet of sleaze with a constant velocity of 50 mm/sec over a coated panel for 3 seconds. The reduction of surface slip is calculated by comparing coefficient of friction from a panel with a modified coating against a panel coated with an unmodified paint (control) in percent (%). The reduction of slip results in a handier surface, which is intended in this application. In addition, the absence of craters in this application is absolutely crucial.

iii. the side chains represent from 0.1 to 95.0 wt.-% based on the total weight of the copolymer,
wherein the (meth)acrylic copolymer has a weight average molecular weight in the range of from 2,000 to 200,000.

2. The copolymer according to claim 1, characterized in that the relative weight ratio of polyether segments and polysiloxane segments in the one or more side chains of the (meth)acrylic copolymer is in the range of from 99:1 to 40:60.

3. The copolymer according to claim 1, characterized in that the amount of polyether segments within the polyether-polysiloxane side chains of the (meth)acrylic copolymer is not lower than 40 wt.-%, based on the total weight of the polyether-polysiloxane side chains of the inventive copolymer.

4. The copolymer according to claim 1, characterized in that it does not contain any urethane groups.

5. The copolymer according to claim 1, characterized in that the copolymer is present in a liquid state at a temperature of 293.15 K and at a pressure of 101.325 kPa.

6. The copolymer according to claim 1, characterized in that the one or more polyether-polysiloxane side chains attached to the (meth)acrylic backbone represent from 1.0 to 50.0 wt.-%, based on the total weight of the copolymer.

7. The copolymer according to claim 1, characterized in that the (meth)acrylic copolymer has a weight average molecular weight in the range of from 5,000 to 100,000 and/or in that the one or more polyether-polysiloxane side chains attached to the (meth)acrylic backbone have a number average molecular weight in the range of from 500 to 10,000.

TABLE 14

Leveling performance and anti-crater properties of inventive surface additives

| Additive | Dosage in wt % on solid | LW | SW | DOI | Slip reduction In % | COF | crater[#] | Surface energy in mN/m total | disperse | polar | Contact angle water in ° |
|---|---|---|---|---|---|---|---|---|---|---|---|
| Control | — | 17.8 | 32.8 | 75.2 | — | 0.21 | 5 | 27.3 | 23.8 | 3.4 | 88 |
| BYK-3560* | 0.1 | 19.5 | 32.4 | 76.8 | −17 | 0.25 | 2 | 26.8 | 22.8 | 4 | 88 |
| B1* | 0.1 | 24.1 | 23.9 | 83.0 | −38 | 0.32 | 1 | 25.7 | 21.8 | 4 | 88 |
| B2* | 0.1 | to many craters, no measurement possible | | | | | | 25.8 | 23.7 | 2.1 | 94 |
| B3* | 0.1 | 28.8 | 23.9 | 82.7 | −31 | 0.30 | 1 | 25.2 | 20.4 | 4.7 | 86 |
| B4* | 0.1 | 62.7 | 80.6 | 70.4 | −39 | 0.30 | 4 | 26.5 | 23.5 | 3.1 | 91 |
| A1 | 0.1 | 22.8 | 23.5 | 79.8 | −31 | 0.28 | 0 | 26.6 | 21.1 | 5.5 | 84 |
| A2 | 0.1 | 19.5 | 24.2 | 79.3 | −26 | 0.27 | 0 | 26.8 | 22.4 | 4.4 | 87 |
| A3 | 0.1 | 27.3 | 24.6 | 79.7 | −5 | 0.22 | 0 | 26.1 | 17.1 | 9 | 76 |
| Control | — | 17.8 | 32.8 | 75.2 | — | 0.21 | 4 | 27.3 | 23.8 | 3.4 | 88 |
| BYK-3560* | 0.3 | 16.4 | 23.0 | 79.6 | −34 | 0.29 | 1 | 27.0 | 21.9 | 5.1 | 85 |
| B1* | 0.3 | 32.3 | 28.8 | 81.3 | −26 | 0.29 | 0 | 25.6 | 18.6 | 7.0 | 80 |
| B2* | 0.3 | to many craters, no measurement possible | | | | | | 26.1 | 24.9 | 1.2 | 98 |
| B3* | 0.3 | 30.7 | 27.2 | 83.1 | −28 | 0.30 | 0 | 25.3 | 17.9 | 7.4 | 79 |
| B4* | 0.3 | 58.2 | 71.2 | 70.2 | −17 | 0.25 | >10 | 26.1 | 23.6 | 2.4 | 93 |
| A1 | 0.3 | 19.5 | 26.2 | 85.3 | −39 | 0.28 | 0 | 29.8 | 18.3 | 13.9 | 68 |
| A2 | 0.3 | 17.3 | 32.3 | 84.1 | −28 | 0.26 | 0 | 27.7 | 19.8 | 8.8 | 75 |
| A3 | 0.3 | 27.0 | 25.9 | 78.6 | 0 | 0.21 | 0 | 31.6 | 13.3 | 18.3 | 61 |

[#]number of craters per panel (50 × 23 cm)

The invention claimed is:

1. A (meth)acrylic copolymer comprising
   a. a (meth)acrylic backbone,
   b. one or more polyether-polysiloxane side chains attached to the (meth)acrylic backbone,
      i. the side chains having a number average molecular weight in the range of from 200 to 20,000,
      ii. the polysiloxane portion of the side chains having a number average molecular weight in the range of from 147 to <1,000, wherein 8. The copolymer according to claim 1, characterized in that it is obtained in that
   (i) at least one polyether-polysiloxane macromonomer containing precisely one ethylenically unsaturated group is copolymerized with at least one further monomer as comonomer, which contains at least one ethylenically unsaturated group, wherein at least one of the precisely one ethylenically unsaturated group of the polyether-polysiloxane macromonomer and of the at least one ethylenically unsaturated group of the comonomer is a (meth)acrylic group, wherein the at least one polyether-polysiloxane macromonomer containing precisely one ethylenically unsaturated group is prepared
(i.1) by a transformation reaction of at least one polyether-polysiloxane macromonomer precursor containing precisely one reactive functional group with an ethylenically unsaturated monomer, wherein the ethylenically unsaturated group of said monomer is retained and incorporated into the formed polyether-polysiloxane macromonomer, or
(ii.2) by a transformation reaction of at least one polysiloxane macromonomer precursor containing precisely one Si—H reactive functional group with a polyether macromonomer precursor containing an alpha-ethylenically unsaturated functional group and an omega-ethylenically unsaturated functional group via a hydrosilylation, wherein the hydrosilylation takes place on the alpha-ethylenically unsaturated group of said polyether macromonomer precursor and the omega-ethylenically unsaturated group of said polyether macromonomer precursor is retained and incorporated into the formed polyether-polysiloxane macromonomer, or in that
(ii) a (meth)acrylic (co)polymer having a (meth)acrylic backbone is formed first by (co)polymerization of at least one monomer containing both a (meth)acrylic group and at least one functional group, and the polyether-polysiloxane side chain or side chains are then attached to the formed (meth)acrylic backbone in a polymer analogous reaction via reaction of said at least one functional group with at least one polyether-polysiloxane macromonomer precursor containing precisely one reactive functional group.

9. The copolymer according to claim 1, characterized in that the (meth)acrylic copolymer is obtained in that
at least one polyether-polysiloxane macromonomer of formula (IV)

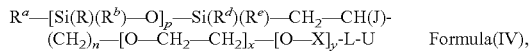

$R^a$—[Si(R)(R$^b$)—O]$_p$—Si(R$^d$)(R$^e$)—CH$_2$—CH(J)-(CH$_2$)$_n$—[O—CH$_2$—CH$_2$]$_x$—[O—X]$_y$-L-U    Formula(IV), wherein
parameter p is in the range of from 0 to 11,
$R^a$ represents a linear, saturated, halogenated or non-halgenated alkyl group with 1 to 30 carbon atoms, a branched, saturated, halogenated or non-halgenated alkyl group with 3 to 30 carbon atoms, an aryl group with 6 to 30 carbon atoms, an alkylaryl group or arylalkyl group, in each case with 7 to 30 carbon atoms, or an alkoxyalkyleneoxide residue or an alkoxypolyalkyleneoxide residue,
$R^b$, $R^c$, $R^d$, and $R^e$ independently of one another represent a linear, saturated, halogenated or non-halogenated alkyl group with 1 to 30 carbon atoms, a branched, saturated, halogenated or non-halogenated alkyl group with 3 to 30 carbon atoms, an aryl group with 6 to 30 carbon atoms, an alkylaryl group or arylalkyl group, in each case with 7 to 30 carbon atoms,
and wherein
$R^d$ may additionally represent [O—Si(R$^b$)(R$^c$)]$_q$R$^a$, wherein $R^a$, $R^b$ and $R^c$ have independently of one another the above defined meanings, and parameter q is in the range of from 0 to 11,
$R^e$ may additionally represent —[O—Si(R$^b$)(R$^c$)]$_o$R$^a$, wherein $R^a$, $R^b$ and $R^c$ have independently of one another the above defined meanings, and parameter o is in the range of from 0 to 11,
wherein the sum of p and q and o is at least=1,
n is =0 to 28,
x=1 to 100,
J is H or denotes $C_{1-4}$-alkyl,
X is selected from propylene and butylene,
y is =0 to x/3,
U is an ethylenically unsaturated head group,
L is —O—, —NH—, —C(=O), —C(=O)—O—, —O—C(=O)—, —NH—C(=O), —(C=O)—NH, a linear O—$C_2$-$C_6$-alkyene radical or a branched O—$C_3$-$C_6$-alkylene radical or a O—$C_3$-$C_6$-cycloalkylene radical,
is copolymerized with at least one further monomer as comonomer, which contains at least one ethylenically unsaturated group,
wherein at least one of the ethylenically unsaturated group U of the polyether-polysiloxane macromonomer of formula (IV) and of the at least one ethylenically unsaturated groups of the comonomer is a (meth) acrylic group.

10. The copolymer according to claim 1, characterized in that the (meth)acrylic copolymer is obtained in that
a (meth)acrylic (co)polymer having a (meth)acrylic backbone is formed first by (co)polymerization of at least one monomer containing both a (meth)acrylic group and at least one functional group, and the polyether-polysiloxane side chain or side chains are then attached to the formed (meth)acrylic backbone in a polymer analogous reaction via reaction of said at least one functional group with at least one polyether-polysiloxane macromonomer precursor of formula (III)

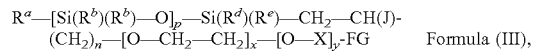

$R^a$—[Si(R$^b$)(R$^b$)—O]$_p$—Si(R$^d$)(R$^e$)—CH$_2$—CH(J)-(CH$_2$)$_n$—[O—CH$_2$—CH$_2$]$_x$—[O—X]$_y$-FG    Formula (III), wherein
parameter p is in the range of from 0 to 11,
$R^a$ represents a linear, saturated, halogenated or non-halgenated alkyl group with 1 to 30 carbon atoms, a branched, saturated, halogenated or non-halgenated alkyl group with 3 to 30 carbon atoms, an aryl group with 6 to 30 carbon atoms, an alkylaryl group or arylalkyl group, in each case with 7 to 30 carbon atoms, or an alkoxyalkyleneoxide residue or an alkoxypolyalkyleneoxide residue,
$R^b$, $R^c$, $R^d$ and $R^e$ independently of one another represent a linear, saturated, halogenated or non-halogenated alkyl group with 1 to 30 carbon atoms, a branched, saturated, halogenated or non-halogenated alkyl group with 3 to 30 carbon atoms, an aryl group with 6 to 30 carbon atoms, an alkylaryl group or arylalkyl group, in each case with 7 to 30 carbon atoms,
and wherein
$R^d$ may additionally represent —[O—Si(R$^b$)(R$^c$)]$_q$R$^a$, wherein $R^a$, $R^b$ and $R^c$ have independently of one another the above defined meanings, and parameter q is in the range of from 0 to 11,
$R^e$ may additionally represent —[O—Si(R$^b$)(R$^c$)]$_o$R$^a$, wherein $R^a$, $R^b$ and $R^c$ have independently of one another the above defined meanings, and parameter o is in the range of from 0 to 11,
wherein the sum of p and q and o is at least=1,
n is =0 to 28,
x=1 to 100,
J is H or denotes $C_{1-4}$-alkyl, X is selected from propylene and butylene,
y is =0 to x/3, and
FG is OH, COOH, epoxy, isocyanate, $NH_2$ or $NHR^a$, wherein $R^a$ is $C_{1-4}$-alkyl.

11. The copolymer according to claim 9, characterized in that the polyether-polysiloxane macromonomer of formula (IV) is copolymerized with at least one further monomer as comonomer, which contains an (meth)acrylic group and is selected from the group consisting of
methyl (meth)acrylate, ethyl (meth)acrylate, n-butyl (meth)acrylate, i-butyl (meth)acrylate, t-butyl (meth)acrylate, lauryl (meth)acrylate, 2-ethylhexyl (meth)acrylate, stearyl (meth)acrylate, behenyl (meth)acrylate, cyclohexyl (meth)acrylate, isobornyl (meth)acrylate, methoxypolyethylene glycol mono(meth)acrylate, hydroxyethyl (meth)acrylate, hydroxypropyl (meth)acrylate and (meth)acrylic acid and mixtures thereof.

12. A process for the preparation of the copolymer according to claim 1, characterized in that said process involves a step, wherein
(i) at least one polyether-polysiloxane macromonomer containing precisely one ethylenically unsaturated group is copolymerized with at least one further monomer as comonomer, which contains at least one ethylenically unsaturated group, wherein at least one of the precisely one ethylenically unsaturated group of the polyether-polysiloxane macromonomer and of the at least one ethylenically unsaturated groups of the comonomer is a (meth)acrylic group,
wherein the at least one polyether-polysiloxane macromonomer containing precisely one ethylenically unsaturated group is prepared
(i.1) by a transformation reaction of at least one polyether-polysiloxane macromonomer precursor containing precisely one reactive functional group with an ethylenically unsaturated monomer, wherein the ethylenically unsaturated group of said monomer is retained and incorporated into the formed polyether-polysiloxane macromonomer,
or
(ii.2) by a transformation reaction of at least one polysiloxane macromonomer precursor containing precisely one Si—H reactive functional group with a polyether macromonomer precursor containing an alpha-ethylenically unsaturated functional group and an omega-ethylenically unsaturated functional group via a hydrosilylation, wherein the hydrosilylation takes place on the alpha-ethylenically unsaturated group of said polyether macromonomer precursor and the omega-ethylenically unsaturated group of said polyether macromonomer precursor is retained and incorporated into the formed polyether-polysiloxane macromonomer,
or wherein said process involves a step, wherein
(ii) a (meth)acrylic (co)polymer having a (meth)acrylic backbone is formed first by (co)polymerization of at least one monomer containing both a (meth)acrylic group and at least one functional group, and the polyether-polysiloxane side chain or side chains are then attached to the formed (meth)acrylic backbone in a polymer analogous reaction via reaction of said at least one functional group with at least one polyether-polysiloxane macromonomer precursor containing precisely one reactive functional group.

13. A composition comprising at least one copolymer of according to claim 1, wherein the composition contains said at least one copolymer in an additive amount.

14. The composition according to claim 13, characterized in that the composition contains the at least one copolymer in an amount of from 0.1 to 10 wt.-%, based on the total weight of the solids content of the composition.

15. The composition according to claim 13, characterized in that the composition is a coating composition, a moulding compound or a cosmetic formulation.

16. The composition according to claim 13, characterized in that the copolymer is applied therein as an additive selected from the group consisting of levelling agents, wetting agents, spreading agents, additives to ameliorate overspray acceptance, anti-cratering agents, surface modification agents, emulsifiers, compatibilizers, hydrophilicity increasing agents, antistatic agents and anti-fogging agents.

* * * * *

UNITED STATES PATENT AND TRADEMARK OFFICE
CERTIFICATE OF CORRECTION

PATENT NO. : 10,035,870 B2
APPLICATION NO. : 15/578357
DATED : July 31, 2018
INVENTOR(S) : Jaunky et al.

Page 1 of 1

It is certified that error appears in the above-identified patent and that said Letters Patent is hereby corrected as shown below:

In the Claims

Column 49, Claim 9, Line 41:
Formula (IV) currently reads:
$R^a\text{-}[Si(R)(R^b)\text{-}O]_p\text{-}Si(R^d)(R^e)\text{-}CH_2\text{-}CH(J)\text{-}(CH_2)_n\text{-}[O\text{-}CH_2\text{-}CH_2]_x\text{-}[O\text{-}X]_y\text{-}L\text{-}U$
Formula (IV)

However, it should be corrected to read:
$R^a\text{-}[Si(R^b)(R^b)\text{-}O]_p\text{-}Si(R^d)(R^e)\text{-}CH_2\text{-}CH(J)\text{-}(CH_2)_n\text{-}[O\text{-}CH_2\text{-}CH_2]_x\text{-}[O\text{-}X]_y\text{-}L\text{-}U$
Formula (IV)

Signed and Sealed this
Fourth Day of June, 2019

Andrei Iancu
*Director of the United States Patent and Trademark Office*